United States Patent
Treat et al.

(10) Patent No.: US 6,908,463 B2
(45) Date of Patent: Jun. 21, 2005

(54) ELECTROTHERMAL DEVICE FOR COAGULATING, SEALING AND CUTTING TISSUE DURING SURGERY

(75) Inventors: Michael R. Treat, New York, NY (US); Fred H. Co, Santa Clara, CA (US); George D. Hermann, Portola Valley, CA (US); Thomas A. Howell, Palo Alto, CA (US); Theodore R. Kucklick, Los Gatos, CA (US); Michelle Y. Monfort, Los Gatos, CA (US); Kenneth H. Mollenauer, Saratoga, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/839,988

(22) Filed: Apr. 20, 2001

(65) Prior Publication Data

US 2004/0073205 A1 Apr. 15, 2004

Related U.S. Application Data

(60) Division of application No. 09/374,563, filed on Aug. 13, 1999, now Pat. No. 6,626,901, which is a continuation-in-part of application No. 09/035,691, filed on Mar. 5, 1998, now abandoned.
(60) Provisional application No. 60/038,589, filed on Mar. 5, 1997.

(51) Int. Cl.[7] .......................... A61B 18/08; A61B 18/10
(52) U.S. Cl. .............................. 606/29; 606/30; 606/31
(58) Field of Search .............................. 606/27–31, 51, 606/52

(56) References Cited

U.S. PATENT DOCUMENTS

| 702,472 A | 6/1902 | Pignolet |
| 728,883 A | 5/1903 | Downes |
| 1,083,386 A | * 1/1914 | Chapman ................... 219/243 |
| 1,422,826 A | 7/1922 | Brown |
| 2,012,937 A | 9/1935 | Beuoy |
| 3,613,682 A | 10/1971 | Naylor |
| 3,625,202 A | 12/1971 | Oysohirhara |
| 3,980,861 A | 9/1976 | Fukunaga |
| 4,031,898 A | 6/1977 | Hiltebrandt et al. |
| 4,196,734 A | 4/1980 | Harris |
| 4,359,052 A | 11/1982 | Staub |
| 4,516,574 A | 5/1985 | Hewes, Jr. |
| 4,587,968 A | 5/1986 | Price |
| 4,654,024 A | 3/1987 | Crittenden et al. |
| 4,662,068 A | 5/1987 | Polonsky |
| 4,702,246 A | * 10/1987 | Ellis et al. .................... 606/31 |
| 5,026,370 A | * 6/1991 | Lottick ........................ 606/42 |
| 5,104,025 A | 4/1992 | Main et al. |
| 5,171,255 A | 12/1992 | Rydell |

(Continued)

FOREIGN PATENT DOCUMENTS

JP 62-127040 9/1987

*Primary Examiner*—Lee Cohen
(74) *Attorney, Agent, or Firm*—Reed Smith LLP; Wiiliam H. Dippert

(57) ABSTRACT

An instrument and method are provided for sealing and joining or hemostatically dividing tissue, which is particularly suitable for laparoscopic and endoscopic surgery. The instrument makes use of the controlled application of a combination of heat and pressure to seal adjacent tissues, to join adjacent tissues, or to anastomose tissues, whereby tissue is heated for an optimal time and at an optimal temperature under optimal pressure to maximize tissue seal strength while minimizing collateral tissue damage. The instrument of the present invention is lightweight and therefore portable, and is particularly useful in field conditions where a source of external power may not be readily available.

10 Claims, 14 Drawing Sheets

U.S. PATENT DOCUMENTS

| | | |
|---|---|---|
| 5,217,460 A | 6/1993 | Knoepfler |
| 5,276,306 A | 1/1994 | Huffman |
| 5,300,065 A | 4/1994 | Anderson |
| 5,336,221 A | 8/1994 | Anderson |
| 5,401,273 A | 3/1995 | Shippert |
| 5,403,312 A | 4/1995 | Yates et al. |
| 5,443,463 A | 8/1995 | Stern et al. |
| 5,445,638 A | 8/1995 | Rydell et al. |
| 5,496,317 A | 3/1996 | Gobel et al. |
| 5,599,350 A | 2/1997 | Schulze et al. |
| 5,624,452 A | 4/1997 | Yates |
| 5,776,130 A | 7/1998 | Buysse et al. |
| 5,810,810 A | 9/1998 | Tay et al. |
| 5,810,811 A | 9/1998 | Yates et al. |
| 5,827,271 A | 10/1998 | Buysse et al. |
| 6,235,027 B1 | 5/2001 | Herzon |
| 6,313,439 B1 | 11/2001 | Fischbach et al. |
| 6,533,778 B2 | 3/2003 | Herzon |
| 6,626,901 B1 | 9/2003 | Treat |

\* cited by examiner

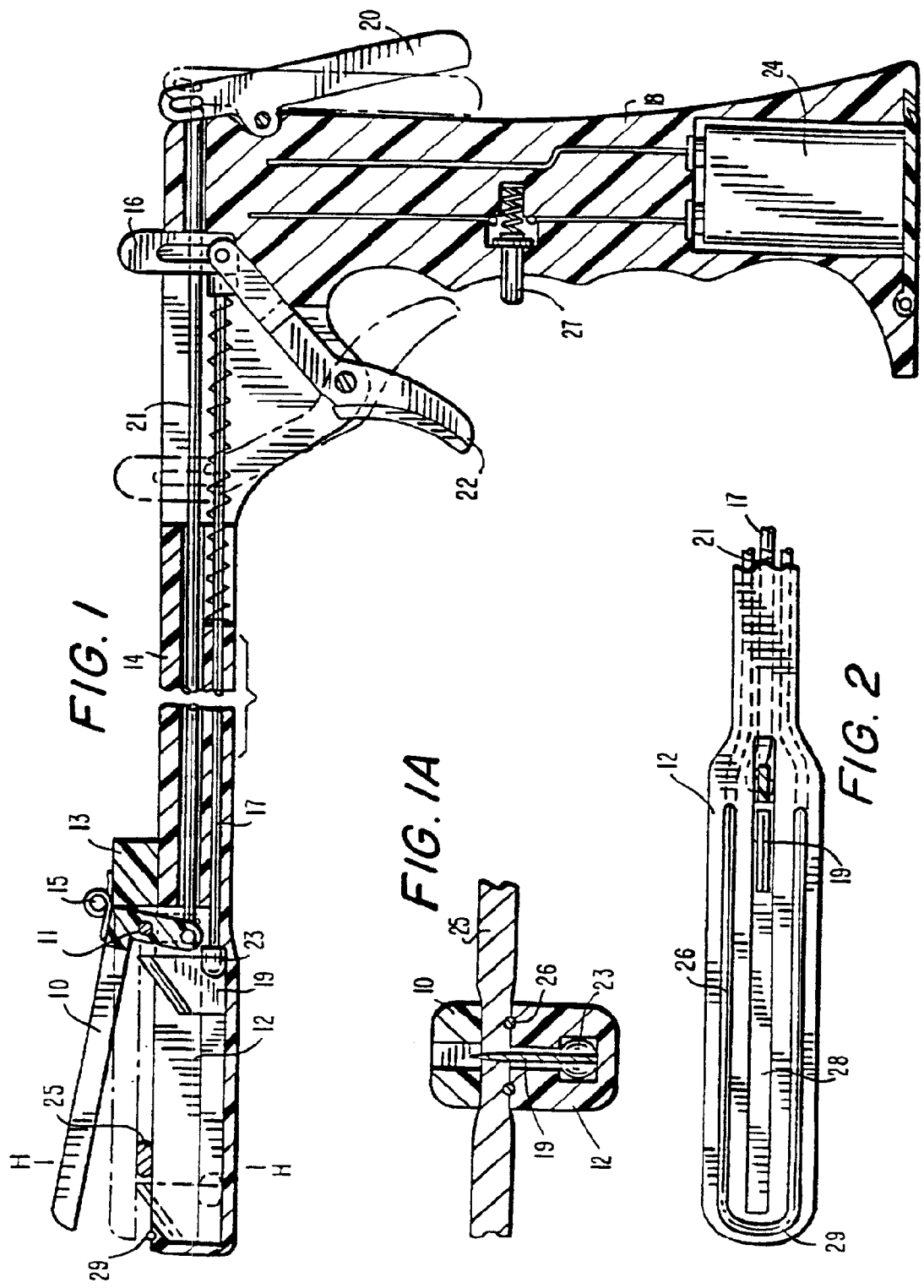

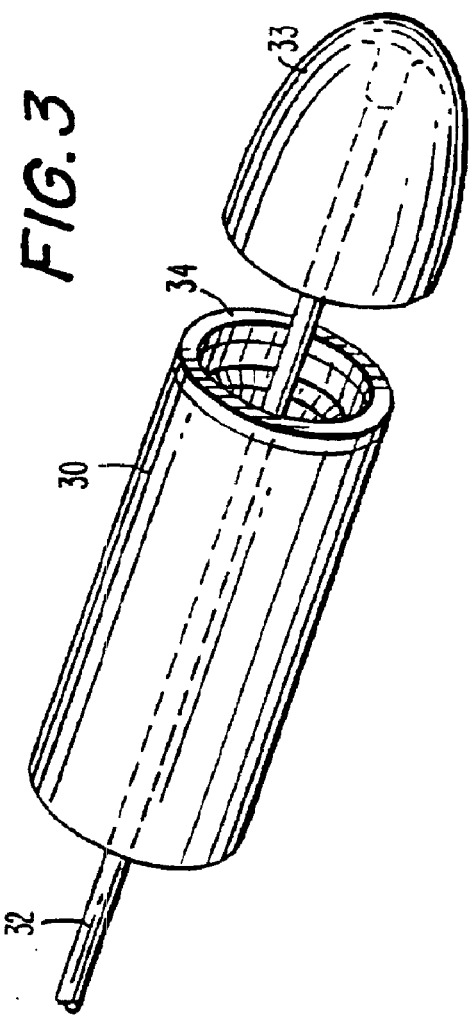
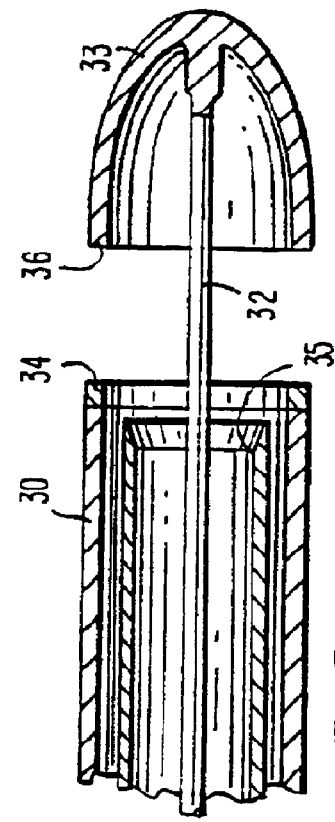
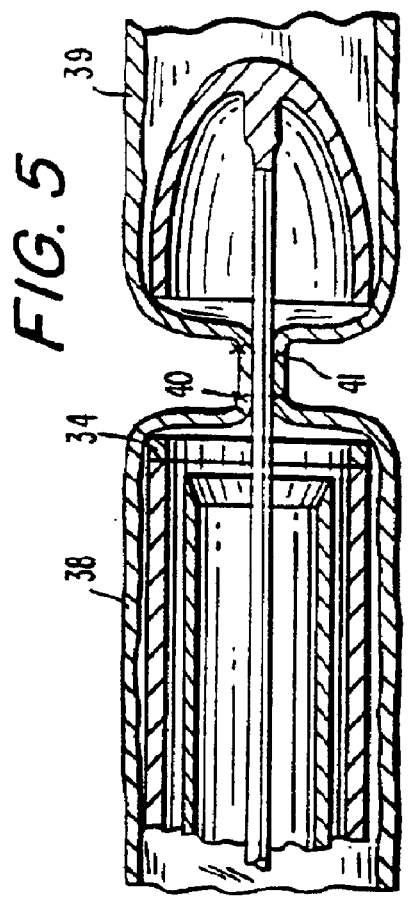

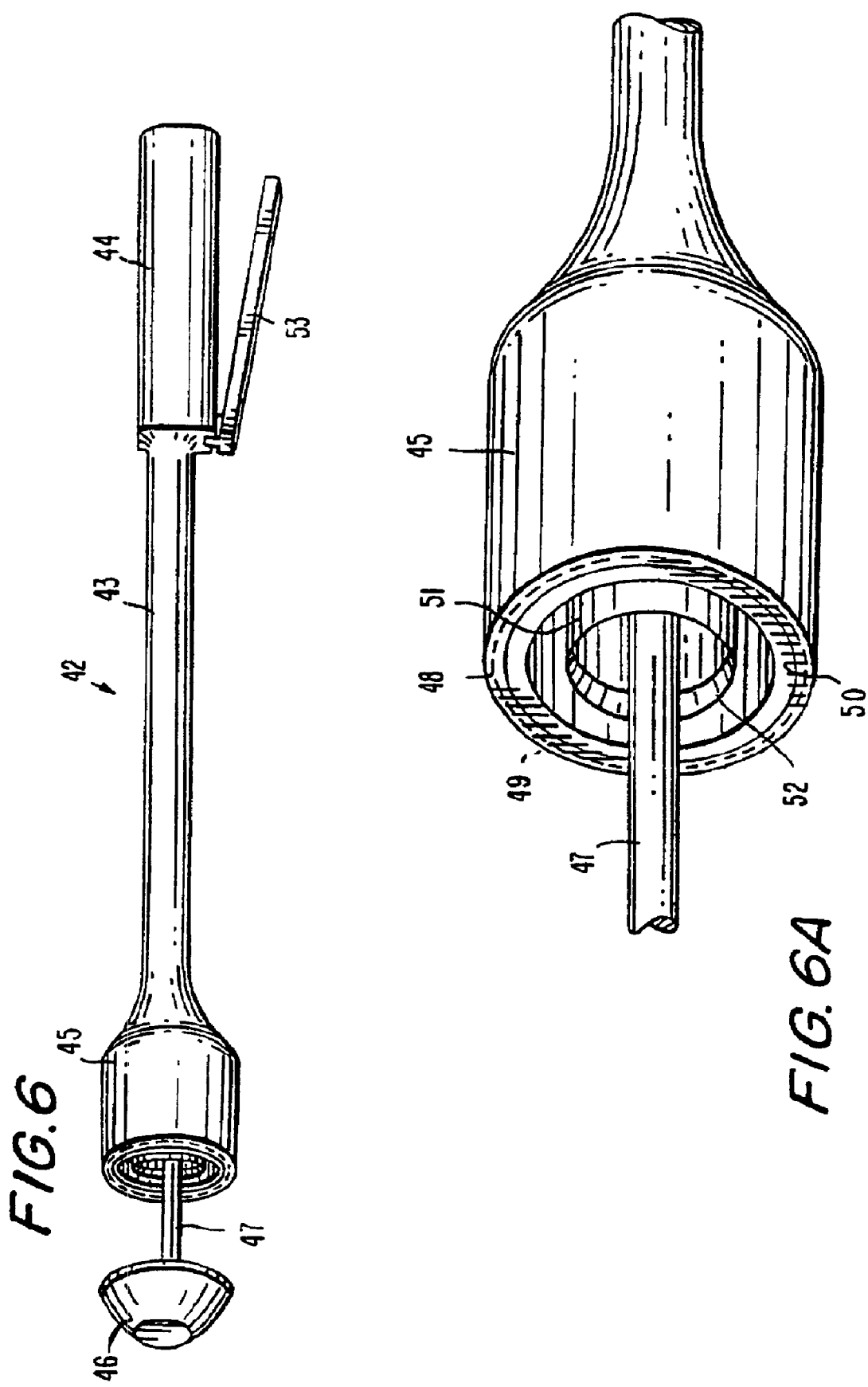

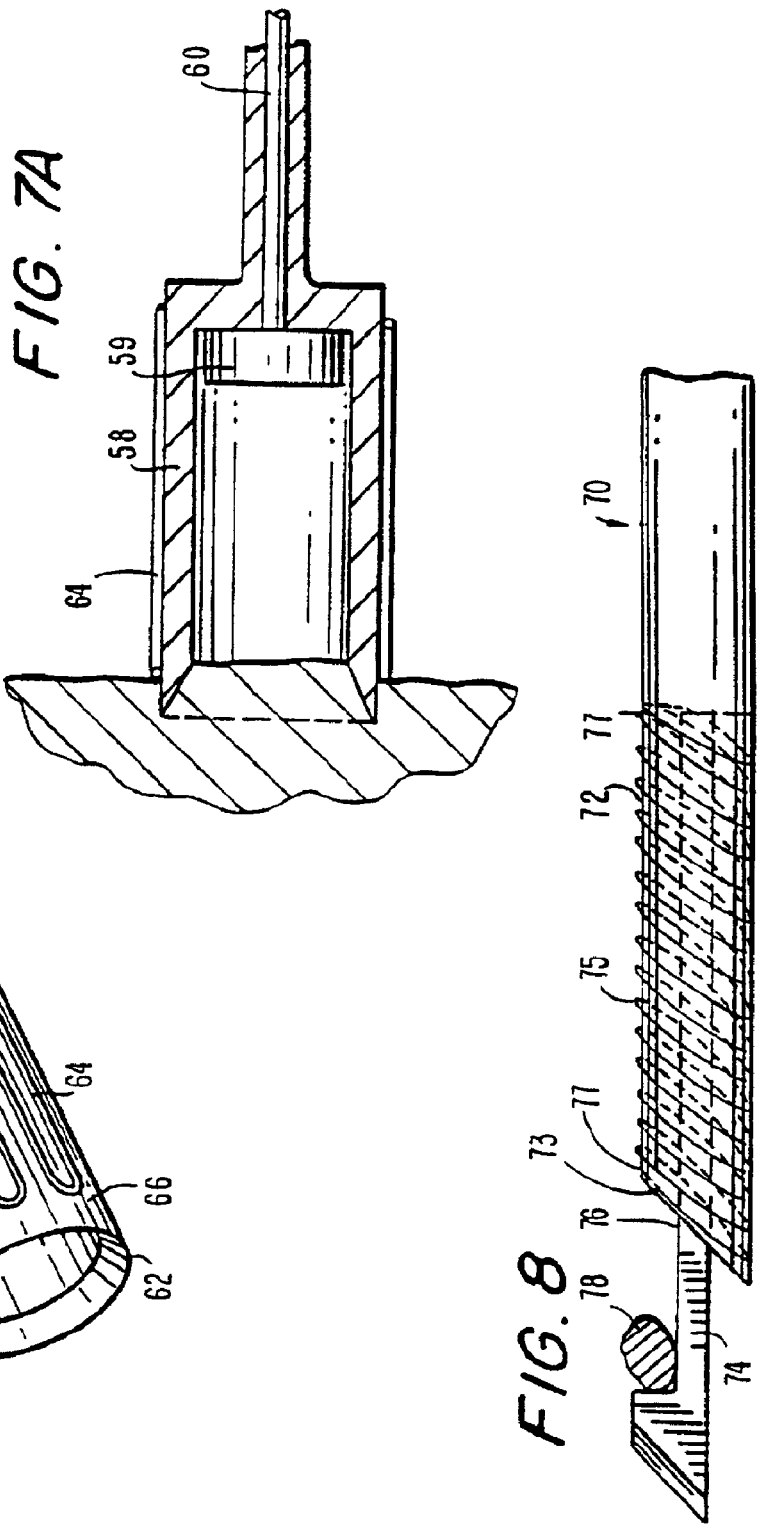

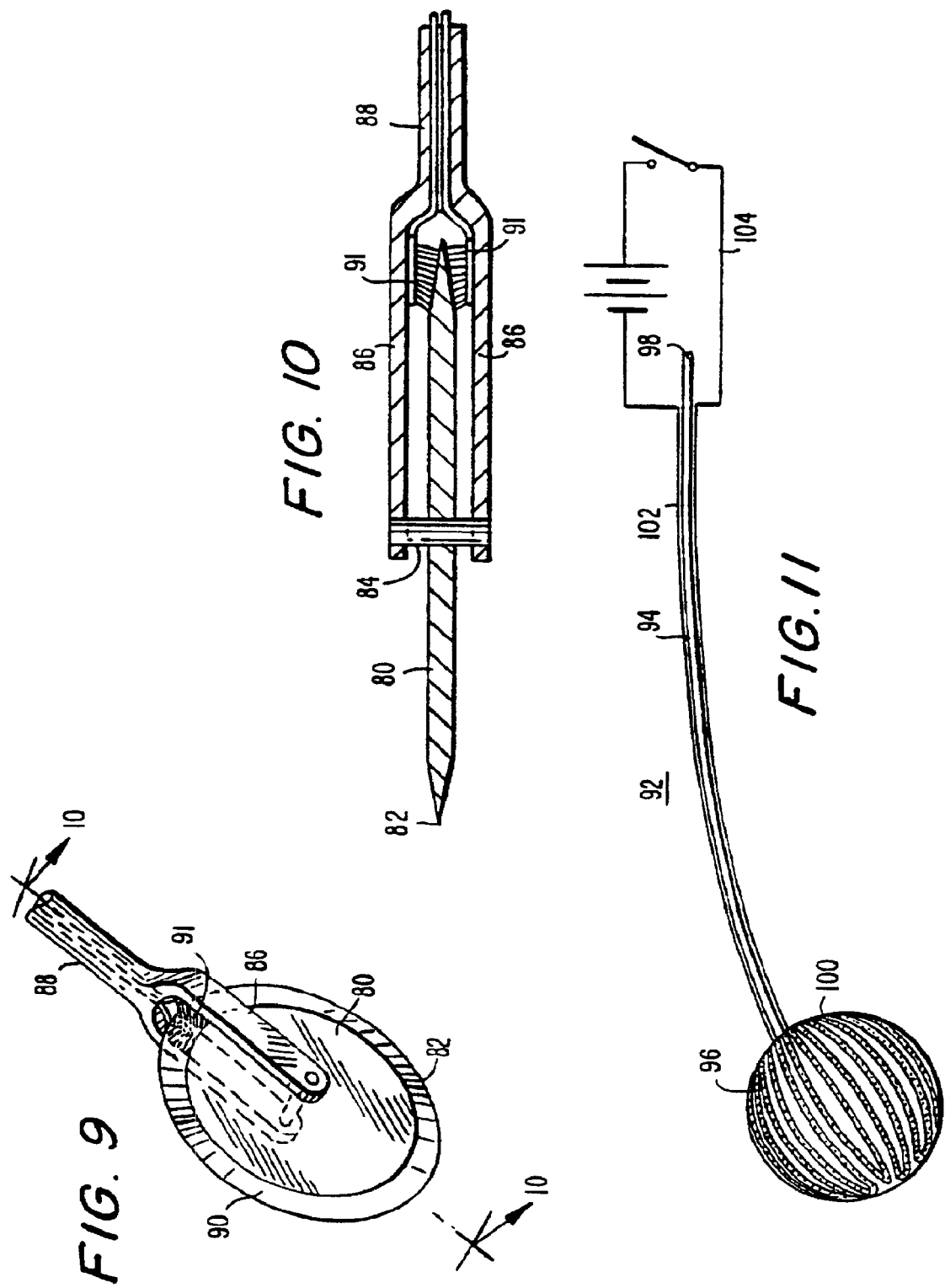

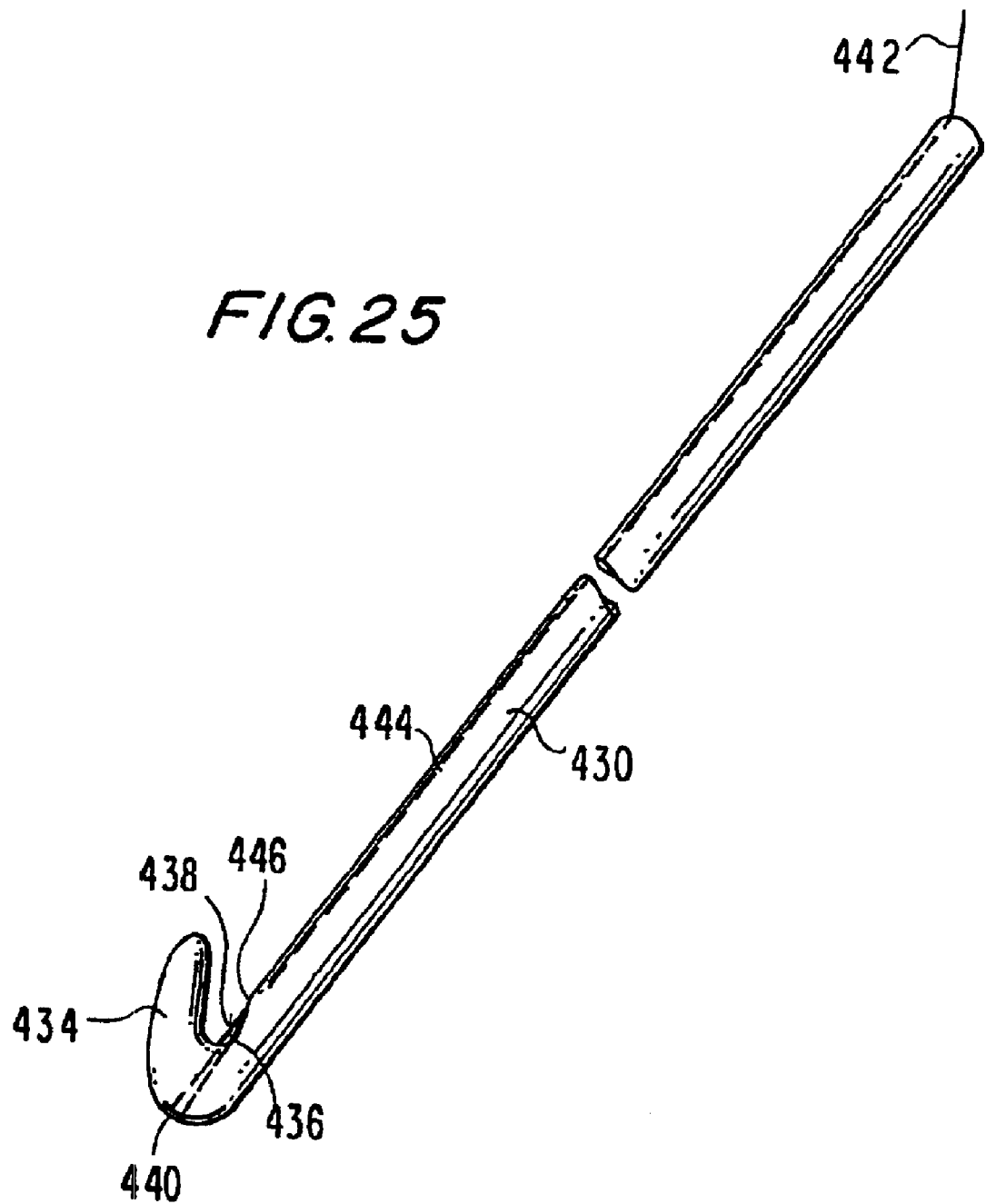

ELECTROTHERMAL DEVICE FOR COAGULATING, SEALING AND CUTTING TISSUE DURING SURGERY

This application is a divisional of U.S. patent application Ser. No. 09/374,563, filed Aug. 13, 1999, now U.S. Pat. No. 6,626,901, which is a continuation-in-part of U.S. patent application Ser. No. 09/035,691, filed Mar. 5, 1998, now abandoned which is based upon U.S. provisional patent application Ser. No. 60/038,589, filed Mar. 5, 1997, all of which are incorporated herein by reference.

FIELD OF THE INVENTION

The present invention relates generally to instruments and methods for sealing and joining or cutting tissue. The instruments of the present invention are especially intended for use during either conventional open surgery or endoscopic or laparoscopic surgery.

BACKGROUND OF THE INVENTION

Hemostasis, or blood clotting, can be obtained by the activation of a naturally occurring biological pathway known as the coagulation cascade. The pathway can be activated by tissue injury. This injury can come from mechanical, chemical or thermal sources. This natural biological pathway results in the conversion of freely flowing blood to a blood clot. Several biological elements are involved in the coagulation cascade, including tissue proteins, mainly fibrin and thrombin. Cells such as platelets and red and white blood cells are also involved.

During surgery, hemostasis can also be achieved by direct denaturization of the proteins found in the blood. Denaturization of a protein means that its characteristic three dimensional structure is altered without actually breaking up the protein. This direct denaturization is a purely physicochemical process in which the denatured proteins bond together, forming an amorphous mass of protein which is comparable to a naturally occurring clot. How does denaturing a protein cause it to stick together with neighboring proteins? Proteins generally have a complex three-dimensional structure. A protein is actually a chain of smaller molecules called peptides, which peptides may have side-chains which contain a molecular group which can attract a molecular group on another side chain. The main protein chain is looped and folded on itself in a complex way which results in the three-dimensional structure characteristic of the protein. This looping and folding occurs because of an intra-molecular attraction between side-chains of the peptides. This attraction between side-chains is generally of the "hydrogen bond" or electrostatic type. The attraction which holds the peptides together along the main chain is a covalent bond. When a protein is denatured, it loses its normal three-dimensional structure. As a result of this unfolding of the protein molecule, the side-chains on the peptides, instead of facing "inward" to fold up the protein chain are now able to bond to side chains from proteins which are neighbors. This inter-molecular bonding results in the formation of a lump of denatured protein. This process is not dependent on the activation of the biological cascades of the natural clotting mechanism, but it is a purely physicochemical process. For hemostasis, the tissue proteins which must be denatured are chiefly those in blood such as hemoglobin and albumin but also include structural proteins such as those found in the wall of blood vessels or in other anatomical structures.

One of the best ways to denature a protein is to heat it up to a temperature high enough to cause the intra-molecular hydrogen bonds to break, but which is not high enough to break the much stronger peptide-peptide covalent bonds along the main chain. A prime example of this process is the heating up of the clear part of an egg until it turns white. This white color means that the original clear protein has been denatured.

Heat which is delivered to tissue proteins may start out as electrical energy, light energy, radio wave energy, or mechanical (vibrational or frictional) energy. As far as the tissue is concerned, it does not matter what the original source of the original energy is, as long as it gets converted in some fashion to heat.

For example, if the source of the energy is a laser, then the light energy is absorbed by molecules in the tissue whose absorption spectrum matches the wavelength of the laser light being used. Once the light energy is absorbed, heat is produced, and the physico-chemical process of protein penetration is achieved. Any sort of light energy will have this effect, if its wavelength is such that it can be absorbed by the tissue. This general process is called photocoagulation. The advantage of using a laser is that since its output is monochromatic, one can selectively heat certain tissue elements which have the right absorption spectrum, while sparing other tissue elements for which the laser light is not absorbed. This principle is used commonly in ophthalmology. Another advantage of using a laser is that its coherent and collimated beam can be very tightly focused on very small targets. If one does not care about spatial precision or selective photocoagulation of only certain tissue elements, then it is perfectly possible to coagulate tissue by using a very bright but otherwise ordinary light.

If the source of energy is electrical currents flowing through the tissue, the process is called "electrosurgery". What happens here is that the current flowing through the tissue heats up the tissue because the tissue has resistance to the flow of electricity ("Ohmic heating"). In the case of ultrasonic coagulation, the rapid vibration of the ultrasonic element induces heating in essentially the same fashion as the production of fire by rubbing sticks together (although the rate of vibration is much much higher and the process is more controllable).

Since it is heat that denatures and coagulates proteins, why go to all the trouble of starting with a laser or an electrosurgery unit? Why not just use a very simple source of heat, such as a resistance wire or, even simpler, a hot piece of metal? In antiquity, "cautery" via a hot piece of iron was used to staunch bleeding wounds. The problem with this approach is not efficacy, it is control and containment of the amount and extent of tissue which is cauterized or injured.

In fact, the development of "electrocautery" in the late 1920's by Professor of Physics William T. Bovie was spurred by the desire (of the pioneering neurosurgeon Dr. Harvey Cushing) to have a more controllable and refined means of producing heat in tissues than possible by using a large piece of heated metal. Electrocautery uses very high frequency alternating electrical current, since it was found that these high frequencies did not cause tetanic ("Galvanic") stimulation of muscle tissue which occurs when direct current or low frequency current is used. To avoid muscular stimulation, it is necessary to use alternating currents with very high frequencies, about several hundred thousand cycles-per-second. This high frequency falls in the range of the AM radio band, which is the reason why many electrical instruments such as monitors used in the OR will register interference when electrocautery is activated. There are many potential problems stemming from the use of such high frequencies, including difficulty in controlling stray currents which can injure patients and interfere with pacemakers and computer equipment. Electrocautery has been refined over the past fifty years, but it still represents a rather round-about way of getting tissue to heat up.

Numerous instruments are known which coagulate, seal, join, or cut tissue. For example, there are electro-surgical instruments, both monopolar and bipolar, which use high frequency electrical current that passes through the tissue to be coagulated. The current passing through the tissue causes the tissue to be heated, resulting in coagulation of tissue proteins. In the monopolar variety of these instruments, the current leaves the electrode and after passing through the tissue, returns to the generator by means of a "ground plate" which is attached or connected to a distant part of the patient's body. In a bipolar version of such an electro-surgical instrument, the electric current passes between two electrodes with the tissue being placed or held between the two electrodes as in the "Kleppinger bipolar forceps" used for occlusion of Fallopian tubes.

There are many examples of such monopolar and bipolar instruments commercially available today from companies including Valley Lab, Cabot, Meditron, Wolf, Storz and others worldwide. A new development in this area is the "Tripolar" instrument marketed by Cabot and Circon-ACM1 which incorporates a mechanical cutting element in addition to monopolar coagulating electrodes.

With regard to known ultrasonic instruments, a very high frequency (ultrasonic) vibrating element or rod is held in contact with the tissue. The rapid vibrations cause the proteins in the tissue to become coagulated. The ultrasonic instrument also employs a means for grasping the tissue while the proteins are being coagulated.

Olympus markets a heater probe instrument which uses an electrical heating wire contained in a catheter type flexible probe meant to be passed through a flexible endoscope. It is used to coagulate small bleeding vessels found on the inside of the gastrointestinal tract or the bleeding vessels found in peptic or other sorts of gastrointestinal ulcerations. In this instrument, no electrical current passes through the tissues, as is the case for monopolar or bipolar cautery. This instrument would certainly not be suitable for use in laparoscopic or open surgery in which large amounts tissue must be not only coagulated but also divided.

There are a number of relevant patents:

Pignolet, U.S. Pat. No. 702,472, discloses a tissue clamping forceps with jaws wherein one has a resistance for heating the jaw, and a battery to power the heater. The coagulated tissue caused by the heat and pressure is subsequently severed along the edges of the jaws before they are opened;

Downes, U.S. Pat. No. 728,883, teaches an electrothermic instrument having opposing jaw members and handle means for actuating the jaws. A resistance member is installed in the jaw member, which is closed to direct contact by a plate. This instrument coagulates tissue by heat, not electrical current, applied to the tissue;

Naylor, U.S. Pat. No. 3,613,682, discloses a disposable battery-powered cautery instrument;

Hiltebrandt et al., U.S. Pat. No. 4,031,898, concerns a coagulator with jaw members, one of which contains a resistance coil. This instrument has a timer mechanism for controlling the heating element. The heating element is used directly as a temperature sensor;

Harris, U.S. Pat. No. 4,196,734, teaches a instrument that can effect both electrosurgery and cautery. A thermistor temperature—sensing element monitors a heating loop and regulates the current and thereby the temperature;

Staub, U.S. Pat. No. 4,359,052, relates to a cautery instrument with removable, battery-powered cautery heating tip;

Huffman, U.S. Pat. No. 5,276,306, discloses a pistol grip, hand-held heating instrument having a trigger mechanism for the battery;

Anderson, U.S. Pat. No. 5,336,221, teaches an optical thermal clamping instrument for welding or fusing tissue, and employing a cutting blade for separating the fused tissue;

Stern et al., U.S. Pat. No. 5,443,463, discloses clamping jaw members that are bifurcated by a cutting blade, having plural electrodes and temperature sensors, and can function as monopolar or bipolar; and Rydell, et al., U.S. Pat. No. 5,445,638, relates to a bipolar coagulation and cutting instrument.

While each of the above-mentioned references is relevant to the invention herein, none teaches or suggests the totality of the invention taught and claimed here.

OBJECTS OF THE INVENTION

It is an object of the present invention to provide a instrument for sealing, cutting, or sealing and cutting tissue.

It is also an object of the present invention to provide a instrument for sealing and joining tissue.

It is another object of the present invention to provide a portable instrument which does not require an external power source.

It is a further object of the present invention to provide a instrument which can be constructed to conform to the requirements of laparoscopic and endoscopic surgery, i.e., to be long and very narrow, in the range of a few millimeters in diameter or even narrower.

It is still another object of the present invention to provide for a method for carrying out surgical procedures using the instrument of the present invention.

It is a still further object of the invention to provide a method and apparatus for optimal heating and optimal pressure to optimize tissue seal strength and to minimize collateral damage to tissue.

These and other objects of the invention will become apparent to one skilled in the art from the following more detailed disclosure of the invention.

SUMMARY OF THE INVENTION

According to the invention, there are three parameters that are independently controlled—the temperature to which tissue is heated, the pressure which is applied, and the time over which the temperature and pressure are maintained. The total heat applied to the tissue is a function of the temperature and the time. A key feature is the combined (simultaneous, partially simultaneous, or sequential) application of pressure and heat to the tissue being coagulated for a specified amount of time, which induces the denatured proteins to bond together, which in turn assists in attaining hemostasis with less heat energy than would be required without the pressure Also, the total energy applied is minimized by means of the configuration and materials of the parts of the instrument that hold the tissue in opposition during the application of the heat and pressure. Using less heat energy means less collateral damage. In addition, results can be achieved that are at least as good as can be achieved with known electro-surgical and ultrasonic tissue coagulation units, but with a much smaller, lighter power source, such as a battery. Also, a very simple and direct method of heating the tissue is used. Since the basic heating element is so simple, the improved results can be achieved at a fraction of the cost of the more round-about means of heating tissue.

According to one aspect of the present invention instruments and methods for sealing, or coagulating, and cutting tissue during surgery are provided. The instruments incorporate means for controllably heating tissue while simultaneously applying a definite and controllable amount of pressure to the tissue being heated. Because of the combined application of heat and pressure, tissue proteins will become coagulated and blood vessels within the tissue will be sealed shut, achieving hemostasis. Optimal sealing or coagulating tissue means producing a strong and durable seal or coagulation or anastomosis with a minimal amount of collateral tissue damage. In the instruments of the invention optimization is achieved by a combination of the physical configuration of the part of the instrument that holds the tissue during the coagulation process and regulation of the time, temperature, and pressure.

As part of the temperature control, heat can be applied in pulses rather than in a continuous manner. Pulsed heat application allows tissue that is adjacent to the area being coagulated time to recover from the heating process and to remain viable. Also, the application of the pressure may be variable in intensity and may also be applied in a pulsed or discontinuous manner.

It is an aspect of the present invention to provide a method and instrument for the surgical treatment of biological tissue, wherein thermal energy and pressure are applied simultaneously, substantially simultaneously, consecutively, or alternatively, over a time such that tissue proteins are denatured and the tissue will adhere or join to itself or to other tissues, for the purpose coagulating bleeding, sealing tissue, joining tissue and cutting tissue. The minimum amount of heat or thermal energy needed to accomplish these goals is expended, so as to minimize thermal damage to tissue adjacent to the treated site.

The instruments of the invention may also incorporate means for cutting, or severing, the tissue after the tissue has been coagulated, "cutting" including dissecting or tissue division, tissue disruption or separation, plane development, or definition or mobilization of tissue structures in combination with a coagulation or hemostasis or sealing of blood vessels or other tissue structures such as lymphatics or tissue joining. The cutting can be achieved by means of a blade which is passed through the coagulated tissue while the tissue is being held in the jaws of the instrument. Cutting can also be achieved thermally by use of amounts of heat greater than the amount required to coagulate the tissues. Alternatively, cutting can be achieved by other mechanical, ultrasonic, or electronic means, including, but not limited to, shearing action, laser energy, and RF, or a combination of two or more of the above. In the case of using thermal energy to achieve tissue cutting, the instruments and methods minimize the amount of energy required to divide tissues with the least amount of unwanted tissue necrosis.

The heating element may be a resistance wire through which electric current is passed, or the heating element may be another material which generates heat when electrical current is passed through it. The electrical current is applied through the wire either as a continuous current or as a series of pulses of definite duration and frequency. Unlike conventional electro-surgical instruments, the electric current of the instruments of the invention does not pass through the tissue, which can cause problems due to stray electric currents. The electrical elements are electrically insulated from the tissue while being in good thermal contact. In a simple embodiment of the instrument, the total amount of continuous current and hence the total heat energy applied to the tissue, is limited in duration by a simple timer circuit or even by direct visual or other sensory inspection of the treated tissue. In a more sophisticated embodiment, the pulse train configuration and duration is under control of a simple microcontroller, such as, for example, an embedded microprocessor. With microprocessor control, a thermistor heat sensor is incorporated into the part of the instrument that grasps the tissue being coagulated. The microprocessor takes temperature readings from the thermistor and adjusts the pulse train configuration and duration to achieve the optimum temperature to cauterize or seal the tissue while minimizing unwanted collateral thermal damage. The actual value of the optimum temperature can be verified experimentally for this particular instrument.

The temperature of the sealing treatment according to one aspect of the invention is preferably kept in the range required to denaturate tissue proteins (approximately 45 C to below 100 C while avoiding excessive necrosis to the tissue. Keeping the temperature in the range required to achieve protein denaturization without excessive tissue necrosis means that the total heat energy expended in the treatment will be less than if the temperature were not kept in this range. The amount of heat energy expended in the treatment is related to the degree of the heat (the temperature) and the length of time for which the heat is applied. The combined application of pressure with the heat reduces the amount of heat or the degree of temperature that would be required to have the denatured proteins actually stick together. This combined application of pressure also increases the strength with which the denatured proteins actually stick together, for a given amount of heat energy at a given temperature.

The amount of pressure applied is regulated by springs or other elastic elements, or mechanically functional equivalents, which will result in the tissue being held with a predetermined amount of force per unit area, in spite of variations in the size or thickness of the tissue being sealed or coagulated. The pressure may also be regulated by mechanical elements or spacers or by the geometry of the pressure producing elements. As with the temperature value, the exact value for the pressure to be applied can be verified for this instrument with appropriate measurement calibration.

The controlled application of a combination of heat and pressure which is sufficient but not excessive to produce a durable coagulation or seal has the result that only a relatively small amount of heat energy is needed. That only a relatively small amount of heat is needed means that relatively small electrical batteries can be used as the energy source to produce the heat. A instrument of the invention can therefore be free of bulky and heavy external power generators such as are required with conventional electro-surgical, laser or other instruments for coagulating tissue. Because small batteries can be used to power the instrument, the instrument can be made quite compact and light weight, as well as portable and/or disposable. The use of batteries or other sources of low voltage direct current facilitates the avoidance of hazards and inconveniences caused by electrical interference and stray currents, which occur in conventional high-frequency electro-surgical instruments. Laser eye hazards are also thereby avoided.

Since the heating elements and pressure producing elements of the instrument may be inherently simple and inexpensive to manufacture, the part of the instrument that comes in contact with tissue can be made in a disposable manner, if desired, while the more expensive portions of the instrument can be made to be reusable. If the instrument incorporates a simple timer, instead of the microprocessor-thermistor controller, the entire instrument including batteries can be made very inexpensively and to be disposable.

Different embodiments of this instrument employing the same general principle of controlled application of a combination of heat and pressure can be used to join or "weld" adjacent tissues to produce a junction of tissues or an anastomosis of tubular tissues. The joining of tissues is essentially a special case of the controlled coagulation of tissue proteins to achieve hemostasis.

It is a further aspect of the present invention that such heat and pressure effects will be spatially confined by the physical configuration and materials employed in the construction of the instrument. The configurations and construction materials are such that (1) the tissue is held in apposition with enough pressure to effect a strong union of the denatured proteins but not enough pressure to cause necrosis of the tissue, and (2) the heat is concentrated on the tissue being treated by means of the material of the jaws which hold the tissue being treated, such material being a thermal insulator which prevents the heat from being expended on heating adjacent tissues. Such material may also employ a reflective layer or coating to reflect back the treated tissue heat energy that would otherwise be lost to thermal radiation. Such material may also have a geometry or be shaped in such a way to focus the thermal energy on the treated tissue and away from tissue not intended to be treated. For example, the jaws of the instrument may have a concave or parabolic inner surface to focus the thermal energy.

It is a further aspect of the present invention that such effects will be spatially confined by the kind, amount, and duration and temporal distribution of the energy delivery. The energy could originate as heat, light, sound or electricity, chemical, or other forms of energy, as long as this energy is converted to heat to denature tissue proteins. In a preferred embodiment, the energy would be delivered from a simple, low cost thermal heating element which could be powered by a battery contained in the instrument itself. The energy could be delivered in a continuous, or pulsed or intermittent mode, at variable or constant intensity. Pulsed or intermittent delivery of energy can produce a spatial confinement of the energy distribution. Feedback (including optical, thermal, spectroscopic, among others) and a microprocessor could be used to control the thermal effect. In the case of tissue coagulating, sealing or joining, the temperatures produced by the energy source could be the range of from about 45 C to about 100 C for a duration long enough to produce denaturation of the proteins in the treated tissue.

The heat or energy delivery source may be a simple electrically resistant wire, straight or curved, a grid or pattern of wires, or a thin-film or coating of electrically resistant material. One or more energy elements may be used. They may target some or all of the tissue treated by the pressure elements. The energy delivery source may be integral with or separate from the pressure elements. Cutting elements may be incorporated into the energy elements. The energy or heat source may move or be fixed. The energy may be delivered in a similar or dissimilar plane compared to the direction of pressure application. The energy or heat source may be constructed in such a way that its shape and size may be varied to conform to different anatomical situations, tissue shapes and thicknesses. For example, an inflatable balloon coated with an electrically resistant material might be employed as the heat source. Another example would be that the heat source might have an expandable f an type configuration which could enlarge ("fan out") to cover a larger surface or a smaller surface as needed. Another example would be a flexible sheet type configuration that could wrap around the tissue to be treated.

It is a further aspect of the present invention that such effects will be spatially confined by the kind, amount, and duration or temporal distribution of the pressure delivery acting in conjunction with the energy or heat source. The delivery of pressure will usually be from a minimum of two elements of the apparatus rather but may in some cases be from simple abutment or pressing of a single element against tissue, as in the example of the circular cutting wheel or a coring biopsy instrument. Any combination of geometric arrangement between the energy source and the pressure source may be produced, including combined energy pressure sources and separate energy and pressure sources. A constant requirement is that the energy element deliver energy to at least some of the tissue that is subjected to pressure by the pressure element. The pressure element likewise may be variable in its shape, being able to adjust its shape before or during the application of the energy or pressure to accommodate for different anatomical situations, tissue shapes or thicknesses. Cutting elements or other elements for shaping or forming the tissue may be incorporated with the pressure element. For example, the pressure element may be comprised of a flattened side with an acute up-angled center to produce a combination of cutting effect over the center with compression along the sides. The pressure applied may be constant or variable over time and the relation of the pressure elements to the tissue may be constant or variable during application of the pressure and energy or both. Motion of the appropriately configured pressure elements may be used to effect cutting before, during or after application of the energy or pressure. The variable application may likewise be controlled by feedback from pressure transducers or strain sensors acting with a microprocessor.

It is a further aspect of the invention that a completely separate cutting element could be used in addition to separate energy and pressure elements. It is also an aspect of the invention that mechanical tissue fastening instruments including sutures, staples, clips, bands, screws, plates or tacks could be incorporated into the instrument. In this case the thermal energy and pressure would be used to provide mainly coagulation and sealing and the mechanical elements would provide additional strength to the tissue joint or anastomosis.

The invention can be used in either open, laparoscopic, endoscopic or any form of minimally invasive surgery. Surgical instruments based on this invention could be long and thin, suitable for laparoscopic or minimally invasive approaches.

The parameters of temperature, time, pressure, as well as the any adjustable physical configuration or geometry of the instrument might vary depending on the type, size, and thickness of tissue being treated. These parameters may be experimentally determined before the actual treatment and incorporated into the instrument by means of a "look-up" table in a microprocessor or by means of simple markings and calibrations of adjustable knobs, dials, etc., of the instrument.

For the purpose of thermally joining or anastomosing two hollow tubular structures, e.g., small blood vessels or vas deferens, a preferred embodiment would incorporate two circular or cylindrical elements. Such cylindrical elements would be designed to fit one into the other, acting as a jug or temporary stent which would hold the two tubular structures together while heat was applied. The tubular structures would be held in such a way to provide either a certain amount of overlap or end-to-end contact. As in previous embodiments, the amount of coaptive pressure which is being applied would be optimized according to the tissue type and thickness. The heat would be provided by a heating element or elements incorporated into the cylindrical jigs or stents and situated to apply the heat to the parts of the two tubular structures which are in overlap or in end-to-end contact. As discussed above, the amounts of heat and pressure applied are the minimum required to produce a secure anastomosis with the least amount of collateral damage.

Another embodiment of this instrument would employ a circular mechanical cutting element, suitable for obtaining "core" biopsies of solid organs such as the liver or a kidney. This circular mechanical cutting element, shaped like a cylinder with sharp edges at one end, would incorporate an electrically resistant element on the outside of the cylinder. This electrically resistant element could be in the form of a thin film of resistance material. As the mechanical cutting of the tissue was done by rotating or pushing the cylindrical cutter into the tissue, hemostasis along the track created by the cutter would be achieved by the heating element on the outside of the cutter. The cylindrical cutter would be constructed out a material, or would incorporate a layer of a material, such that the tissue core sample being removed would be insulated from the thermal effects of the heating element on the outside of the core. This design would allow for retrieval of tissue samples which are not distorted by heat changes and also allow for secure hemostasis along the tract of the biopsy. In this instrument, the lateral pressure exerted by the cylinder wall on the tissues of the track cannot be explicitly controlled; however, there is pressure, and this pressure is part of attaining hemostasis.

In a further embodiment of the invention, a circular cutting wheel would be mechanically rotated to cut tissue, such as skin. This circular cutting wheel would incorporate along its rim, an electrically resistant thin film. This electrically resistant element would provide for hemostasis as the rotating mechanical wheel cuts the tissue.

In a yet further embodiment of the invention, an inflatable elastic balloon could be used to apply heat and pressure to tissue. The exterior surface of the balloon would be coated partly or totally with flexible, optionally stretchable, electrically resistant material that will heat up when electrical current is applied. Here, the pressure exerted on the tissue can be controlled by regulation of the inflation pressure of the balloon.

Another embodiment of the invention comprises a compact electrical cutting and coagulating instrument which allows blood vessels, other vessels in the body, or organ tissue to be divided with electrical energy while at the same time being ligated by heat-induced coagulation. This embodiment comprises a forceps or tweezer-like gripper with two arms which may grasp a vessel or section of organ tissue with gripping areas at the tip of the arms. One arm is fitted with a protruding cutting wire, while the other arm is provided with an anvil surface and, optionally, a recess for receiving the cutting wire. Cutting a vessel or tissue is accomplished by heating the wire and closing the tweezer arms on the vessel or tissue, allowing the hot wire to cut the vessel or tissue. Sealing the vessel or tissue is accomplished when the tweezer arms have closed upon the severed ends of the vessel, whereupon the anvil surface is heated to cause coagulation of the vessel or tissue. The wire may be made of a non-stick composition comprising carbon, and the anvil may comprise non-stick substances such as PTFE or carbon. The cutting wire is heated to a high temperature from an electrical power source, preferably a DC power source, and preferably powered by batteries housed in the body of the instrument or in a portable battery pack. The anvil may be heated by radiant and conductive heat from the cutting wire, with heating wires powered from the electrical power source, or from the cutting wire indirectly.

Optionally a standard clamp can be modified to accept a cartridge containing a heating element and a power supply, or an instrument useful for laparoscopic procedures may be the functional equivalent of the forceps described above.

The instruments of the invention can be used in surgery and are particularly well suited to laparoscopic and endoscopic surgery. Because the method described uses heat energy in the minimum amount and at the lowest temperature consistent with attaining denaturation and sticking together of tissue proteins, instruments which work based on this method will be able to function more efficiently than conventional surgical energy instruments. Therefore these instruments can be portable and even battery powered, which makes them ideally suited for portable or military applications.

There is no instrument or method in the prior art which specifically seeks to obtain surgical coagulation, sealing, joining or cutting by a combination of resistant heat energy and pressure at a time, temperature and pressure which together are sufficient but not excessive to produce protein denaturization, and with a physical configuration and materials of construction which promote the sticking together of the tissues being treated while min losses of heat energy to surrounding tissues beyond the treatment zone.

BRIEF DESCRIPTION OF THE DRAWINGS

Reference is made to the following description taken in connection with the accompanying drawings, in which:

FIG. 1 is a schematic representation of one embodiment of the present invention;

FIG. 1A is a cross-section along line I—I of the embodiment in FIG. 1 with the Jaw in closed position;

FIG. 2 is a top, partly cross-sectional view of the lower jaw of the embodiment of FIG. 1 showing the heating and cutting elements;

FIG. 3 is a plan view of another embodiment of the invention;

FIGS. 4 and 5 are cross-sectional views of the embodiment of FIG. 3;

FIGS. 6 and 6A are a plan view and a partial, enlarged view, respectively, of a further embodiment of the invention;

FIGS. 7 and 7A are a plan view and a partial cross sectional view, respectively, of another embodiment of the invention;

FIG. 8 is a partly cross-sectional view of a further embodiment of the invention;

FIG. 9 is a plan view of yet another embodiment of the invention;

FIG. 10 is a top, partly cross-sectional view of the embodiment of FIG. 9;

FIG. 11 is a plan view of another embodiment of the invention for heating and cauterizing tissue;

FIGS. 24 and 25 are each a schematic, partially cross sectional view of another embodiment of the invention adapted for laparoscopic use.

DETAILED DESCRIPTION OF THE INVENTION

Figure 12:
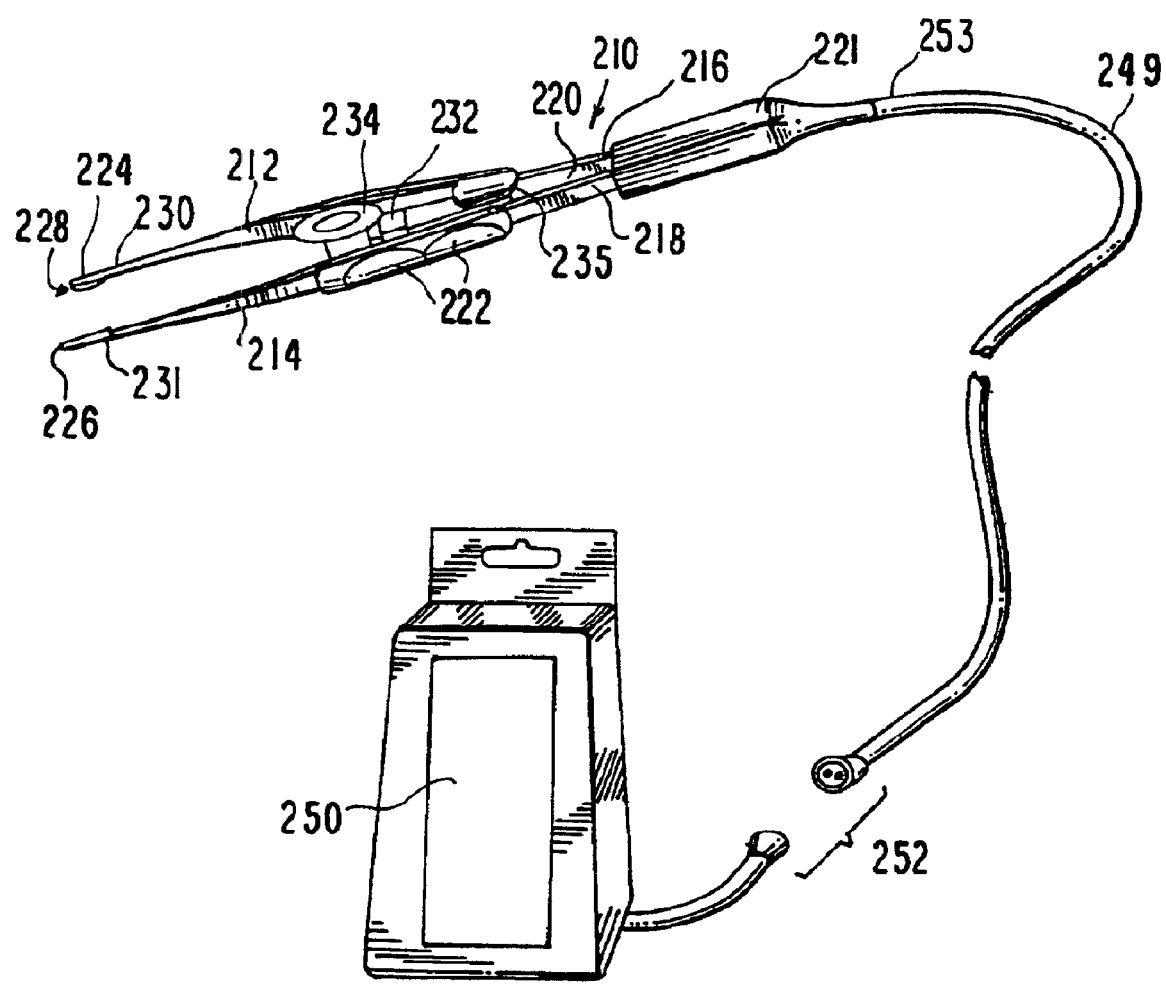
FIG. 12 is a prospective view of a forceps embodying a cutting and/or coagulating element in accordance with the invention.
Figure 13:
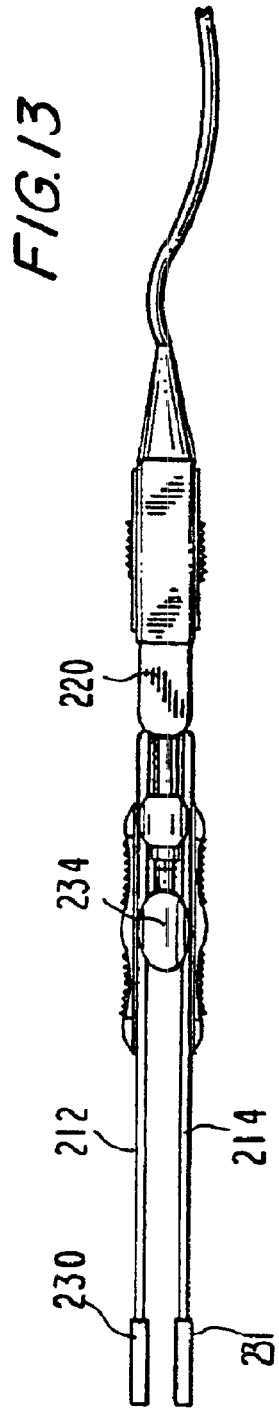
FIG. 13 is a top view of the embodiment shown in FIG. 12.
Figure 14:
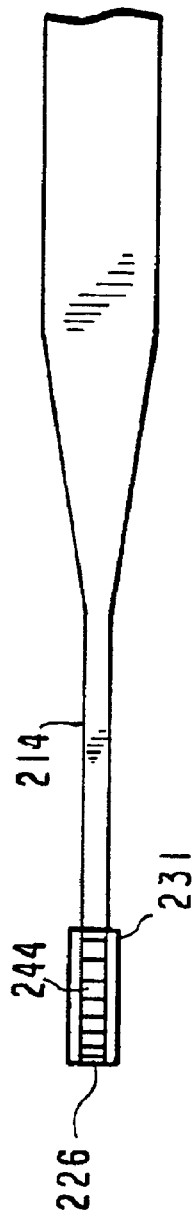
FIGS. 14 and 15 are each partial views of a forceps arm from the embodiment shown in FIG. 12.

The invention can perhaps be better appreciated from the drawings. FIG. 1 depicts a schematic representation of the instrument of the invention showing an upper jaw 10, a lower jaw 12, an elongated shaft 14 attached to a handle 18, having a lever 20 for opening and closing the jaws. Upper jaw 10 is attached at hinge 11 to spring support member 13, and spring 15 is attached to both upper jaw 10 and spring support member 13 to bias upper jaw 10. Lever 20 is operatively connected through rod 21 to one or both of upper jaw 10 and lower jaw 12. The end of shaft 14 closest to handle 18 is provided with (1) a pusher 16 which is operatively connected through member 17 and connector 23 to a cutting knife blade 19 housed in lower jaw 12 and (2) a trigger 22 to actuate pusher 16 which in turn actuates cutting blade 19. The lower end of handle 18 is provided with a rechargeable battery pack 24, which is operatively connected to heating element actuator 27 and heating wire element 26 in lower jaw 12.

In FIG. 1A, tissue segment 25 is clamped between jaws 10, 12, where it can be cut by blade 19.

FIG. 2 depicts a top view of lower jaw 12 showing the relative locations of heating wire element 26 and a slot 28 for cutting blade 19, within jaw 12. Heating wire element 26 is in a groove of a depth such that the wire is substantially flush with the surface of jaw 12. Preferably the distal portion 29 of heating wire element 26 is below, or out of, the plane of heating wire element 26 so that only two parallel areas of tissue will be sealed. Heating wire element 26, which preferably is comprised of nichrome or another suitable electrically resistant metal or alloy, or an electrically resistant thin-film or coating will preferably have a suitable, thermally conductive, electrically resistant, non-stick coating. Examples would include polytetrofluoroethylene (PTFE), e.g., TEFLON®, or other nonstick coatings used in cookware. Moreover, one or both of the facing surfaces of upper jaw 10 and lower jaw 12 may optionally be corrugated, irregular, or grooved.

Both the upper and lower jaws are composed of a material, such as ceramic, which is thermally insulating or thermally reflective. In this way, the heat generated by the heating element is confined to the space between the jaws, and is not allowed to spread or radiate to other tissues that may be in contact with the outside of the jaws. This is beneficial in two ways: first, the heat generated by the heating element is used efficiently to perform the desired sealing or coagulation, and second, surrounding tissues are protected from inadvertent thermal injury.

s would be appreciated by one skilled in the art, the heating, pressure, and/or cutting functions could be mechanically, electromechanically, or electronically synchronized to obtain optimal results according to the invention. Also, the instrument shown in FIGS. 1, 1A, and 2 may optionally not have a cutter element. Such a instrument would be intended for situations where only heating and pressure would be necessary to join tissue or to otherwise heat and cauterize tissue to produce coagulation.

In the embodiment of the invention shown in FIGS. 3 and 4, a cylindrical member 30 is concentrically positioned around a rod 32, the distal portion of which forms anvil 33. The distal surface of cylindrical member 30 comprises a circular heating element 34 and a circular cutting element 35 arranged concentrically within heating element 34. Anvil 33 is configured so that when rod 32 is moved proximally, the proximal circular edge 36 of anvil 33 cooperates with heating element 34 to coagulate or seal tissue.

Use of the embodiment of FIGS. 3 and 4 can be appreciated in FIG. 5, where, for example, two sections of intestine 38,39 are positioned to be joined together. Initially one end of each of sections 38,39 is loosely connected with ligatures 40,41 about rod 32. Then, rod 32 is moved distally to cause circular edge 36 of anvil 33 to force portions of intestines 38,39 into contact with heating element 34. Intestine sections 38,39 are joined together, and excess tissue is cut off by cutting element 35. Rod 32 is then pulled further in the proximal direction to remove the excess tissue, cylindrical member 30, and anvil 33.

In addition, the instrument shown in FIGS. 3 to 5 to produce circular anastomosis by relying on heat and pressure could additionally incorporate mechanical fastening elements such as staples. Such a instrument is shown in FIGS. 6 and 6A, where a circular stapling instrument 42 comprises a main shaft 43, a handle 44, a staple housing 45, and an anvil 46. Anvil 46 is fixedly attached to the distal end of anvil shaft 47, which is movably slidable within staple housing 45, main shaft 43, and handle 44.

The distal surface 48 of staple housing 45 has slots 49 for staples (not shown) and an electrically resistant coating or member 50. An inner circular member 51 with a cutting edge 52 is arranged circumferentially around anvil shaft 47, as can be seen more clearly in FIG. 6A. Optionally, slots 49 and coating 50 could be coextensive so as to facilitate direct heating of the staples.

Handle 44 comprises means for operating anvil 46 and heating element 49 and for firing the staples. As would be appreciated by those skilled in the art, a staple firing lever or member 53 can be operatively connected to a cylindrical pushing member within stapling housing 45 that causes the staples to be ejected from slots 49.

The operation of the circular stapling instrument would be similar to that of instrument shown in FIG. 3, with the exception that staples would be fired into tissue to be joined. Preferably the staples would be fired subsequent to sealing and concurrently with the cutting. The staples would act in conjunction with the thermal energy to enhance the strength of the tissue seal, joint or bond while the thermal energy would enhance the hemostatic capability of the staples. Staples or other mechanical tissue fasteners could be used in conjunction with thermal energy sealing in configurations other than circular, such as linear or angled.

FIG. 7 depicts an embodiment of the invention that is essentially a tissue-core removal instrument. The tissue core removal instrument 56 comprises a cylindrical member 58 having a fixedly attached proximally extending handle 60. Cylindrical member 58 comprises a sharp cutting edge 62 and a heating element 64 arranged on the outer surface 66 of cylindrical member 58. Optionally, sharp cutting edge 62 could be replaced by a heating element to do the cutting.

Consistent with the description above, a tissue sample is obtained by inserting removal instrument 56 into an organ, with instrument 56 being rotated as it moves forward. The rotation could be either clockwise or counterclockwise, but preferably alternatingly clockwise and counterclockwise, with sufficient pressure to cause edge 62 to cut. Heating element will cauterize or seal tissue adjacent to the tissue 64 sample to be removed, and when a tissue sample of sufficient depth is positioned within cylinder 58, instrument 56 will be removed. As is conventionally done, removal instrument 56 would preferably contain means for removing a tissue sample, such as an internal piston 59 having a proximally-extending actuator 60 to force the sample to be ejected from the distal end of removal instrument 56. As would be appreciated by those skilled in the art, a tissue-core removal instrument may optionally have additional cutting means at its distal end to assist in separation of a core tissue sample from the tissue mass.

In FIG. 8 the distal portion 70 of an electrothermal biopsy needle comprises an outer cutting sheath 72 slidably circumferentially arranged around an inner slotted stylus 74 having a slot 76 to capture a tissue sample 78. The outer sheath 72 has a cutting edge 73 which separates tissue sample 78 from the rest of the tissue mass (not shown) and encloses sample 78 in slot 76 when outer sheath 72 is propelled distally by an actuator (not shown).

Outer sheath 72 preferably has an electrically resistant film 75 coating on its distal portion. Film 75 may have spaced-apart electrical contacts or connectors 77. In another embodiment of a biopsy needle where stylus 74 has an inner cutting member (not shown), the stylus or the inner cutting member, or both, may have an electrically resistant coating or film.

The aforementioned aspect of the invention could be incorporated into known biopsy instruments. See, for example, U.S. Pat. Nos. 4,600,014 and 5,595,185, both of which are incorporated herein by reference with regard to their descriptions of biopsy instruments.

FIGS. 9 and 10 depict a circular cutting embodiment of the invention in which a disk 80 having a sharp outer edge 82 is attached at its center to a rod 84 which is rotatingly secured to forks 86 of handle 88. Adjacent edge 82 is a circular heating element 90, which can be on one or both surfaces of disk 80. Each heating element 90 is electrically connected to fork 86, for example, through one or more brushes 91. Optionally, sharp cutting edge 82 could be replaced by a circumferential heating element to do the cutting.

FIG. 11 represents an embodiment of the invention where a heating and cauterizing instrument 92 comprises a catheter 94 and an inflatable balloon 96 sealingly attached to the distal end of catheter 94. Catheter 94 comprises at least one lumen 98, which is in fluid communication with balloon 96 for inflation and deflation. The proximal end of catheter 94 is in fluid communication with a regulated pressure source or inflation source (not shown) for inflating and deflating balloon 96.

Balloon 96 has an electrically resistant film coating 100, at least two separate portions of which are connected to wires 102 that extend proximally along or within catheter 94 to a power source 104. The electrically resistant film coating 100 is intended to cover a substantial portion, if not all, of the outer surface of balloon 96.

In use, instrument 92 with a deflated balloon 96 is manipulated within a patient's body, e.g., intracorporeally or even percutaneously, to position balloon 96 adjacent to a site to be cauterized. Then, balloon 96 is inflated so that the electrically resistant film coating 100 contacts the area to be cauterized, whereupon film coating 100 is energized with electrical energy from source 104. After the heat and pressure produce the desired effect, the power is turned off and the balloon is deflated to facilitate removal.

With regard to the embodiments of the invention depicted in FIGS. 3 to 11, it should be appreciated that the respective heating elements are electrically connected to an appropriate power supply. It is envisioned that in each instance the power supply can be a battery or battery pack, which can be fixedly attached or integral with to the respective instrument. Optionally, the battery or battery pack could be separately mounted or positioned, such as on a clip or belt means for the operator to wear. It is within the scope of the invention that other standard sources of electrical power, such as transformers, may also be used. Other sources of heat such as fuel, e.g., butane, or chemical reactions, may be used.

As mentioned above, one aspect of the invention concerns optimization of (1) thermal energy application, i.e., temperature and time, and (2) pressure, i.e., force and duration, to achieve maximum tissue seal strength and minimal collateral tissue damage. Those skilled in the art will appreciate that useful parameters will vary greatly.

However, in practical application to human tissue a voltage of from about 0.5 volt to about 14 volts, preferably from about 1 volt to about 12 volts, will be applied to a heating element having a resistance sufficient to generate thermal energy to heat tissue to a temperature adequate to cause denaturation of proteins. This temperature is in the range of about 45° C. to about 100° C. The pressure applied would be sufficient to provide coaptation but less than would crush or destroy the tissue itself.

The strength of tissue coagulations, seals, anastomoses or welds can be experimentally measured. For example, the strength of a coagulation produced on the side of a lacerated blood vessel can be measured experimentally by first producing the coagulation and then applying measured amounts of hydrostatic pressure to the inside of the vessel until the coagulation blows off and bleeding recommences. The strength of a tissue weld can be measured by first joining two pieces of tissue together and then placing the joined tissues in a machine which attempts to pull the tissue apart with increasing and measured amounts of force. Collateral thermal damage is also a measurable quantity in that the amount of collateral thermal damage can be readily assessed visually or microscopically. By use of this methodology, a table of optimized parameters could be constructed for any type of tissue. These parameters would be incorporated into the various instruments by means of selecting the voltage, current, and resistance of the heating elements and also the amount of pressure used to press the tissue together during the coagulating/sealing/joining process, as well as the time duration of the process. These parameters can simply be incorporated into the instrument (i.e., simple mechanical timer, fixed preset voltage and current, and spring-loaded pressure instruments, or, we can incorporate more flexible and active controls based on microprocessor regulation of the heating process, guided by a "look-up" table in ROM and by using sophisticated mechanical force/pressure sensors and strain gauges) . Also, for certain applications, it may be sufficient to have a skilled operator, visually or by other sensing means, determine the duration of energy application and the amount of pressure required.

The instruments of the present invention may be constructed of any suitable material, such as will be familiar to one skilled in the art, for example, out of a reinforced engineered plastic such as fiberglass reinforced polycarbonate, or machinable or injection-molded ceramics, or high temperature glass or epoxies, or mica. Alternatively they may be constructed out of a suitable alloy steel such as 318 stainless steel, or the like. The heating element may be a simple resistive wire or may be a thin film or coating composed of metallic, organo-metallic, or organic materials which may be conducting or semi-conducting. The actual materials of construction will be a matter of choice depending upon whether the instrument is to be employed repetitively or in a disposable manner. Indeed, in the latter situation it is contemplated that different parts of the instrument may be constructed of metal alloy and/or plastic, in which situation the plastic disposable components can be thrown out after each use and the more expensive metal alloy components reused. If sophisticated and expensive control circuitry is used, this part of the instrument could be made in a reusable manner.

FIG. 12 illustrates an embodiment of a forceps instrument 210 which may be variously described as a pincer or tweezers. Forceps instrument 210 comprises forceps arms 212 and 214, the proximal ends 216 and 218, respectively, of which are attached to switch housing 220. The outer surfaces of forceps arms 212 and 214 contain finger grips 222 to assist the operator in holding and activating forceps instrument 210. An optional sleeve 221 covers the proximal portion of housing 220.

Forceps arms 212 and 214 may be formed of a suitable resilient material such as stainless steel, for example, that has the desired combination of stiffness and spring rate. For disposable applications forceps arms 212 and 214 may be formed from a homogeneous plastic material, or a material that is filled with particulate material to increase stiffness or abrasion resistance.

Alternatively, forceps arms 212 and 214 may be formed from a composite material tailored to provide the desired stiffness according to specific functional and ergonomic needs and to provide heat resistance for electro-surgical and thermosurgical applications. The composite material may be any composite construction, e.g., fiber material, glass, carbon fiber, Kevlar, aramid, or metallic particles bound with an epoxy, polyester, or other resin, forming the composite matrix.

Forceps arms 212 and 214 may be manufactured in a unitary construction, via casting, lay-up, compression molding, lamination, or molding of a pre-impregnated fiber cloth in a manner known to one skilled in the art. The forceps arms may also be molded or cut from pre-formed sheet composite material and glued or riveted together. Components may also be filament wound. Alternatively the components may be stainless steel with a flex circuit.

The composite matrix may also have molded into it conductive wires or strips for transmission of electrical energy or transmission of data signals. The carbon in the carbon fiber matrix may also be used to conduct electrical or data signals. The fiber in the matrix, which may be carbon, glass, Kevlar, aramid, or other fiber, may be laminated such that the unidirectional fibers are oriented at an angle to one another to achieve the desired spring rate and stiffness characteristics.

Figure 15:
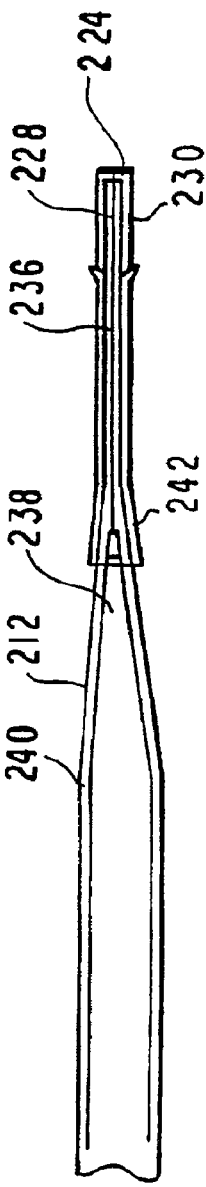
Figure 16:
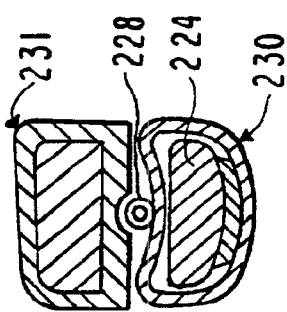
FIG. 16 is a cross-sectional view of the distal portions of the forceps arms shown in FIG. 12.

One or both of the distal ends 224 and 226 of forceps arms 212 and 214, respectively, contain a heater wire 228, as shown in greater detail in FIGS. 15 and 16. Each of said distal tips 224 and 226 comprises a non-slip sleeve or "bootie", such as heater sleeve 230 on distal tip 224 and anvil sleeve 231 on distal tip 226, which sleeves may be comprised of clear or opaque, deformable, resilient, non stick material. Suitable materials include polytetrafluoroethylene (PTFE), available as TEFLON@, graphite, KAPTON, mica, or silicone. Each sleeve 230,231 evens out pressure against tissue and insulates the surfaces of forceps arms 212 and 214 electrically and thermally. Sleeves 230, 231 may also incorporate thermally reflective material as layers or coatings. Useful reflecting materials would include ceramics, thermally reflective metals, or thermally reflective polymers, such as MYLAR@ polymeric compositions. Sleeves 230,231 also prevent heat dissipation and focus heat from heater wire 228 on a specific area, while spreading the heat sufficiently to obtain a good seal zone. By insulating and reflecting, i.e., managing, the heat generated by heater wire 228, sleeves 230,231 minimize power consumption to achieve the intended result. Also, the resiliency of sleeves 230,231 is intended to lengthen the useful life of heater wire 228, which becomes fragile when hot.

Switch housing 220 comprises a finger-operated switch 232, e.g., a multi-directional post-in-tube design, preferably a high current, low voltage switch. When a button 234 is pushed into the plane of forceps arms 212 and 214, from either direction, switch 232 is activated so that current is provided to heater wire 228. When button 234 is released, the button returns to its starting position and the flow of current is interrupted. Optionally, housing 220 comprises at least one anti-swivel guide 235 to form a channel to help maintain forceps arms 212 and 214 parallel to one another. In addition, the forceps may be used with a foot-activated switch instead of a finger-activated switch. The same switch housing may be used, but without a finger switch. Instead, the circuit may be completed by depressing a foot switch that is connected via an electrical cable between the battery pack and the forceps power cord.

In a preferred embodiment of the invention switch housing 220 comprises circuitry to control or manage the current supply to heater wire 228. This circuitry, known generally as an "actuator" is an important and useful feature. Deterioration of heater wire 228 is prevented by contact of heater wire 228 with the heat sink of the pinched tissue and the opposing forceps arms. The presence of the actuator induces the operator to apply a minimum amount of pressure to the closed forceps distal tips, which insures good sealing/welding of the vessel or organ tissues. In addition there is the important safety aspect that the actuator prevents inadvertent exposure of heating wires to drapes or other flammable materials in the operating room, should the finger-operated switch be inadvertently activated.

As can be seen more clearly seen in FIG. 15, at least one distal tip of one of the forceps arms, such as distal tip 224 of forceps arm 212, comprises heater wire 228 on the outer surface of heater sleeve 230, preferably with a slight gap between distal tip 224 and heater sleeve 230, which gap could be filled with a fluid such as a gas or liquid. This provides for additional thermal insulation between heater wire 228 and forceps distal tip 224. Heater wire 228 may comprise any useful electrically resistant, preferably non-stick material such as nichrome or an alloy thereof, graphite, nitinol, stainless steel, platinum, or tungsten, uncoated or coated with a non-stick material such as graphite. In fact, any material may be used such that the heater wire 228 has a lower Ohmic resistance than body tissue. This lower resistance allows the resistive element to be exposed but not transfer electricity through the tissue. The length, diameter and material selection are adjusted to optimize sealing and cutting. Although heater wire 228 preferably has a round smooth surface, wire 228 may be other then round and have a textured surface to increase traction. A flat surface would be better for sealing applications, whereas a pointed surface would be better for cutting applications. It is within the scope of the invention that heater wire 228 may be a flex circuit or just a very flat wire. While heater wire 228 is shown in FIG. 12 as being substantially straight, heater wire 228 could instead be curved or arcuate.

Heater wire 228 is connected by solder to broader, flat wire 236, which is in turn soldered to the distal portion 238 of a copper strip laminated to the inside surface 240 of forceps arm 212. Flat wire 236 is covered by a polymeric sleeve 242.

Distal tip 226 of forceps arm 214 comprises sleeve 231 having a thicker inner surface 244, which inner surface 244 may comprise an integral part of sleeve 231 or a separate component that has been adhered to the inner surface of sleeve 231. In a preferred embodiment of the invention, said inner surface 244 comprises a separate polymeric member or surface that has been glued or fused with sleeve 231, optionally with molded ridges on the surface facing heating wire 228 to improve grip/tissue traction. Optionally sleeve 230 comprises a gripping inner surface so that the gripping surfaces are generally perpendicular to a plane defined by forceps arms 214, 216.

Heater wire 228 is electrically connected through cord 249 to a power source such as a battery pack 250. Battery pack 250 can comprise any number of commonly available batteries (such as D cells or AA cells), dependent upon application. Battery pack 250 may optionally comprise sensing circuitry and a vibrating or auditory alarm to indicate a "low battery" situation, to minimize sticking and peeling of tissue when the battery is low and heater wire 228 would not be hot enough to seal or cut. Preferably, there will be a tone from housing 230 or battery pack 250 to indicate the forceps has been activated, with another tone or vibration to indicate that the battery is low. While there could be a cutoff rather than a low battery signal, it is believed that a low battery signal is preferable. It is intended that the battery pack will be capable of being clipped to the operator's uniform or suspended on an IV pole, or otherwise positioned in a convenient location adjacent the treatment area. Preferably the battery pack is connected to instrument 210 with a releasable connection 252 so that battery pack 250 can be readily replaced. The proximal portion of sleeve 221 may comprise a swivel connection 253 with cord 249.

The preferred power source is a steady DC battery pack. It is within the scope of the invention that the power source could be a wall outlet plug-in transformer of steady DC, pulsed DC, low frequency AC, or even RF. One could also provide for a cutoff ability, for example, in the event of a short circuit or wire break, and/or a temperature feedback, optionally with a control to minimize temperature for sealing and maximizing temperature for cutting. Also, optionally there would be a feedback to power capability to automatically adjust for use under liquid conditions, e.g., saline, versus non-liquid conditions, to reduce the risk of wire burnout.

In the event that the power supply has DC/RF capability, the forceps can also function as an RF instrument. If the distal tips of the forceps arms were closed and then tissue was contacted, the RF/forceps would act like a hemostatic electrode or blade. Optionally a sleeve could be removed and replaced with a Bovie blade. (Also, the instrument could be activated with a dedicated hand switch or a foot switch.)

Figure 17:
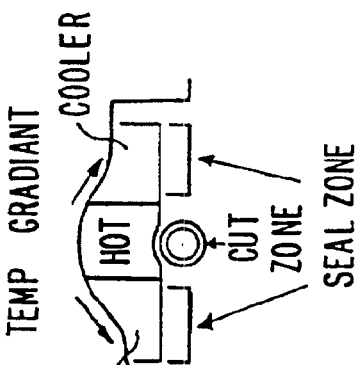
FIG. 17 is a graphic representation of the temperature gradient of tissue heated with the embodiment of FIG. 12.

A primary application of the forceps instrument shown in FIGS. 12 to 16 is to seal and cut tissue such as blood vessels, other corporeal vessels or ducts, corporeal organs, and vascularized tissue. It is also useful for sealing in the lymphatic system. The way in which said forceps works can perhaps be appreciated by referring to FIG. 17, which comprises a representative graph of the temperature gradient in a vessel or tissue ("tissue") to which this instrument is applied. At the portion of tissue in direct contact with or immediately adjacent to a heater wire, the temperature of the tissue will be very hot—sufficiently hot to sever the tissue. At the same time, at the areas of tissue immediately adjacent to and roughly parallel to the "cut zone", the tissue will be heated but not to the same extent as in the cut zone. In these two secondary areas, each referred to as a "seal zone," tissue will be cauterized and sealed. This tip configuration allows for expedient division and sealing of blood vessels or vascularized tissue with the simple process of closing the forceps arms and momentarily applying heat energy at the forceps tips. This process will divide and seal the tissue. Additionally, when the tissue is gripped under moderate traction, the tissue will often automatically fall away from the jaws of the forceps as the heating element divides and seals the tissue. Heat from the heating element conducts laterally into the adjacent tissue while it is being compressed within the forceps tips. As a result, this tissue is often completely sealed by the time it is divided and falls away from the forceps jaws. This way, the divided tissue will not bleed as it is divided. The surgeon moves to a new area of tissue to be divided hemo-statically, and this simple process is repeated. With this approach to cutting and coagulation, significant time and materials can be saved, reducing the need for applying clips or ligatures, or for the use of other hemostasis products or techniques. Thus, with this particular embodiment of the invention, tissue can be cut and cauterized with one fairly simple repetitive motion.

Figure 18:
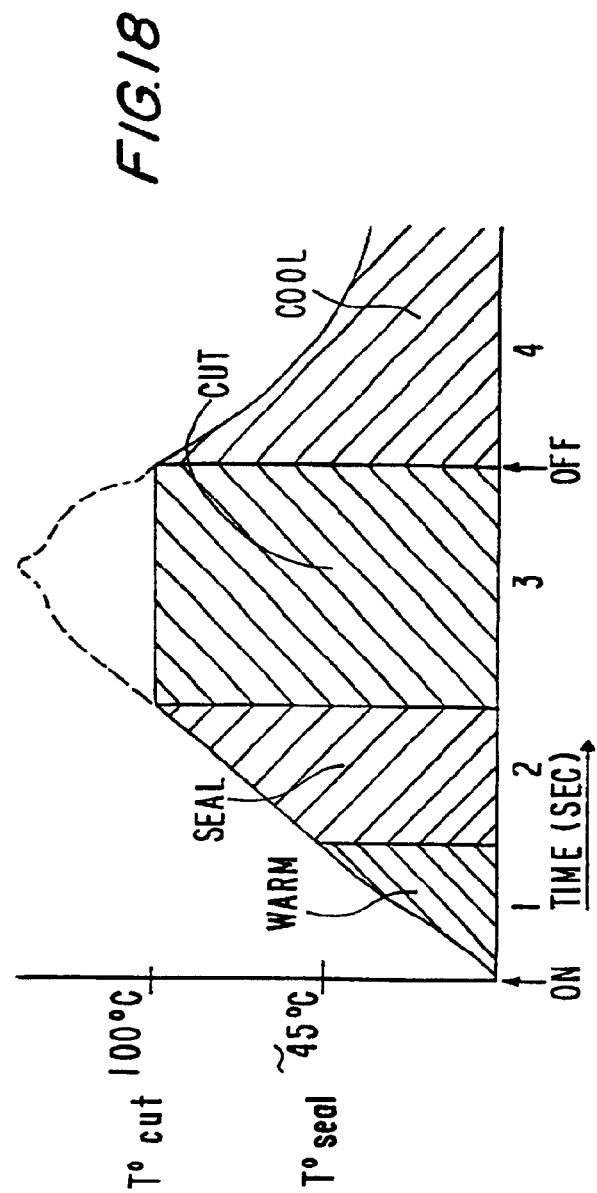
FIG. 18 is a graphic representation of the time vs. temperature characteristics of the embodiment of FIG. 12.

The time vs. temperature graph shown in FIG. 18 illustrates the principles involved behind the process of sealing and cutting with the forceps device. After tissue is grasped between the forceps tip, the heat is activated by the button 234 at t=0. As the heating element heats up, heat is conducted into the tissue being grasped. As the temperature increases with time, the tissue passes the temperature value necessary for sealing and hemostasis (and eventually approaches the temperature necessary for dividing the tissue). Tissue closer to the heater is hotter than tissue farther away from the heater. Eventually (typically at t=2 to 5 seconds) the tissue immediately adjacent to the heater becomes hot enough that it divides. This division usually occurs after the tissue slightly farther away from the heater has reached a sufficiently elevated temperature for sealing and/or coagulation to occur there. Alternatively a pre-programmed "lock out" interrupts the power supply, so that the tissue remains at the appropriate temperature for the appropriate time, for example, 100° C. for approximately one second, whereupon the tissue is severed and then cools.

Figure 19:
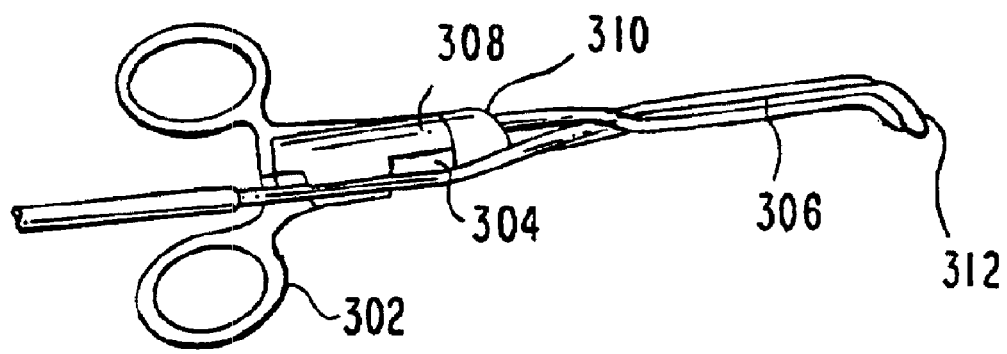
FIGS. 19 and 20 are prospective views of a clamp embodiment of the invention.
Figure 20:
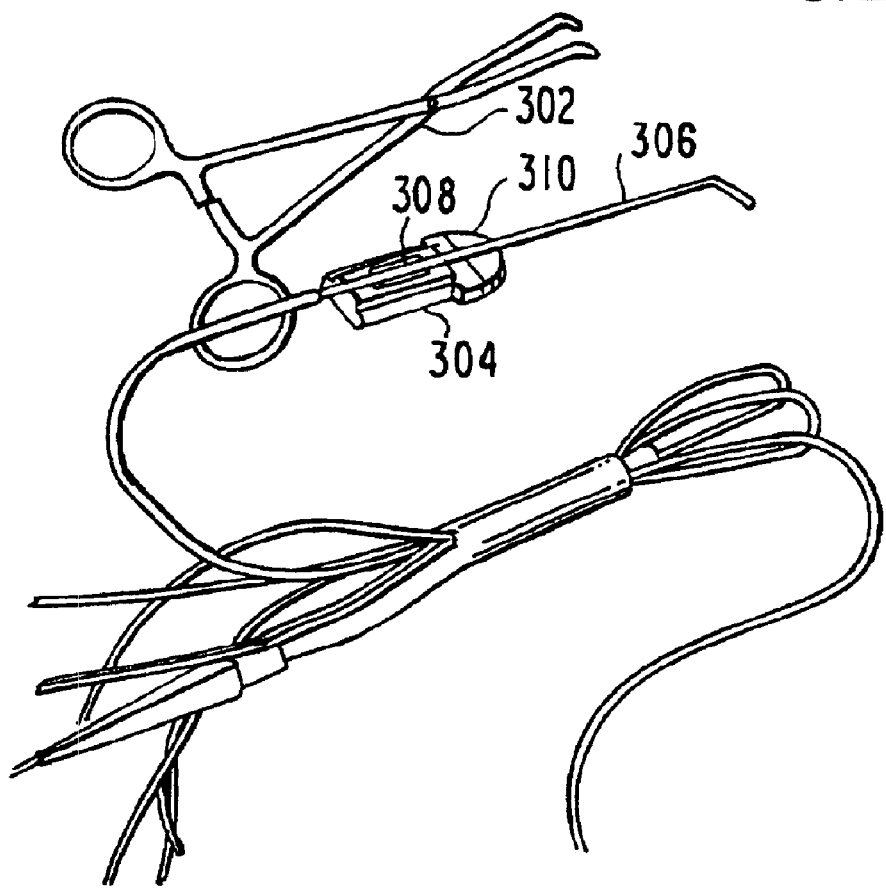

In the embodiment of the invention set forth in FIGS. 19 and 20, a clamp 302 comprises a cartridge 304 that can be removably attached to clamp 302. Clamp 302 is essentially a common surgical clamp that has been adapted to receive cartridge 304. Cartridge 304 comprises an elongated member 306 having a switch housing 308 with a switch activator 310. The distal end of member 306 comprises a heating element 312 that is in electrical connection with switch housing 308 and a power supply (not shown).

Figure 21:
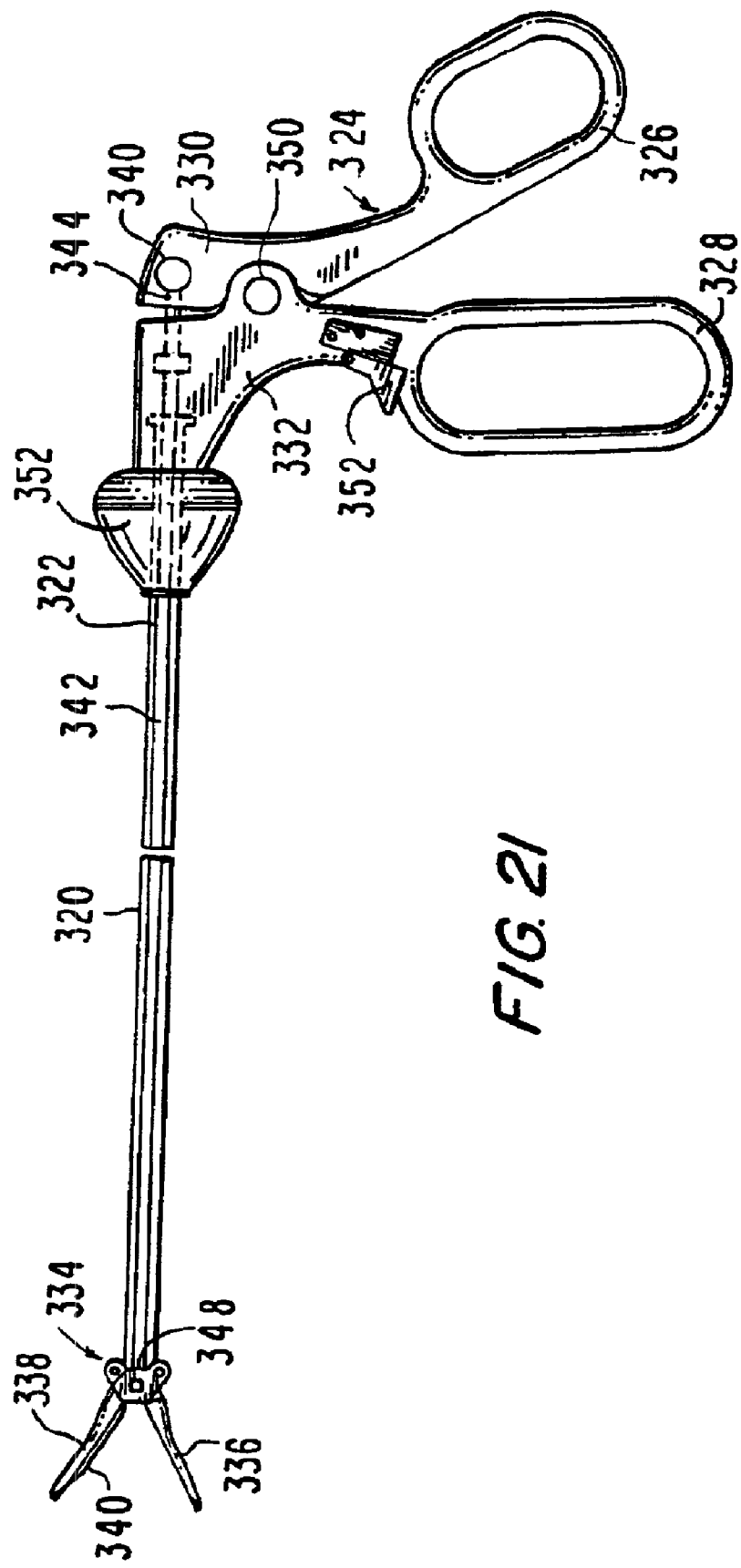
FIG. 21 is a perspective view of an embodiment of the invention specifically adopted for laparoscopic use.

The embodiment of the invention shown in FIG. 21 is a modification of the embodiment shown in FIGS. 12 to 16 intended for laparoscopic application. According to this embodiment an elongated member 320 is attached at its proximal end 322 to a handle 324 housing comprising hand grips 326 and 328 attached to grip members 330 and 332, respectively. The distal end 334 of elongated member 320 comprises gripping arms 336 and 338, at least one of which has a heating element 340. Gripping arms 336 and 338 may optionally have sleeves (not shown).

An actuator rod 342 has a proximal end 344 rotatively attached to grip member 330 at fastening point 346, and the distal end 348 of actuator rod 342 is operatively connected to gripping arms 336 and 338. Grips 326 and 328 and their respective grip members 330 and 332 are movably connected at pivot point 350, so that when grip 326 and 328 are squeezed together, proximal end 344 moves proximally and gripping arms 336 and 338 move together. A rotating positioner 352 can rotate to in turn rotate elongated member 320 and gripping arms 336 and 338.

Grip member 332 preferably contains a finger-activated switch 352 to control the flow of electricity to heater wire 340.

Figure 22:
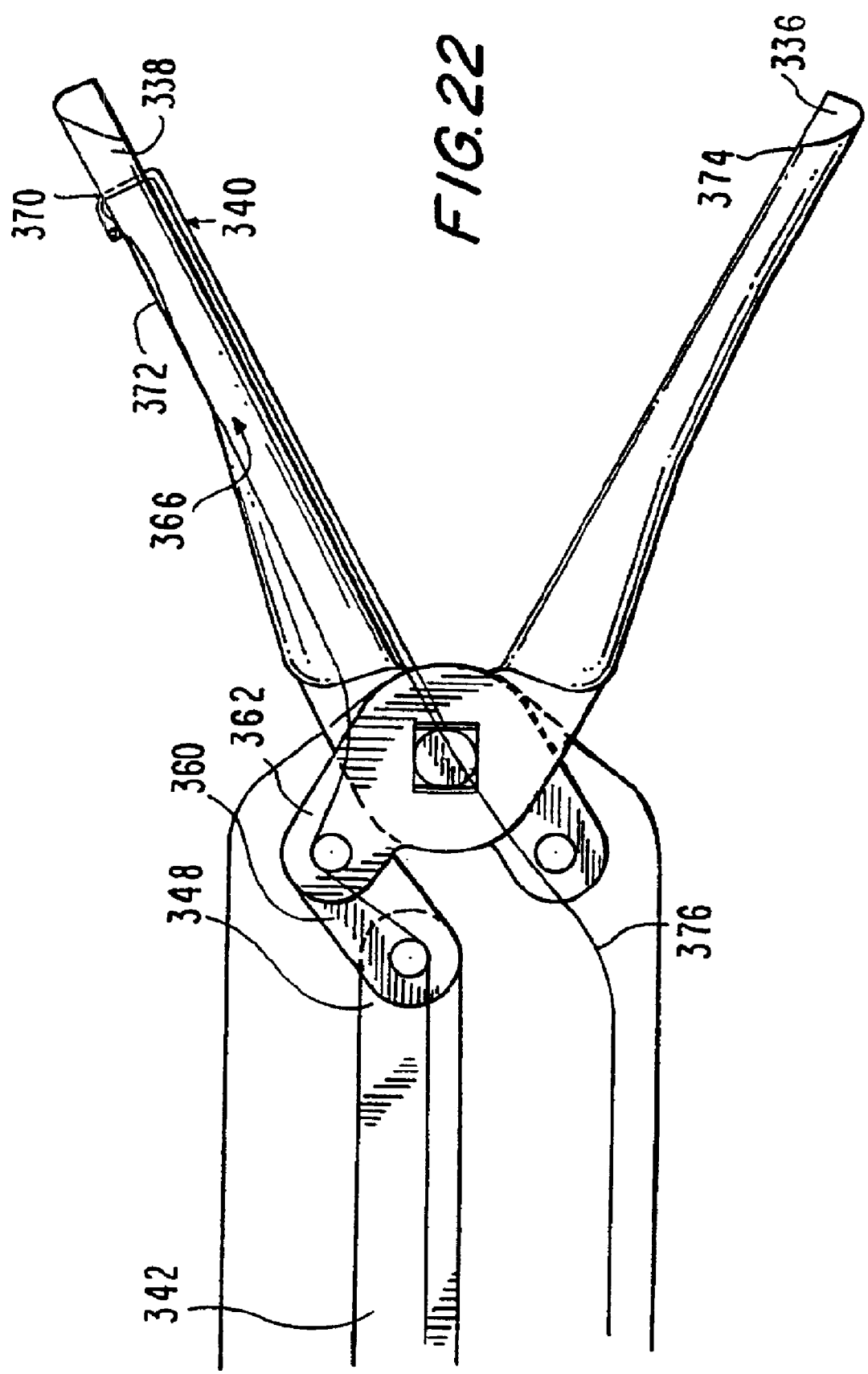
FIG. 22 is a partially cross-sectional view of the distal end of the embodiment shown in FIG. 21.

In FIG. 22 one embodiment of the operative connection between actuator rod 342 and gripping arms 336 and 338 is shown. Distal end 348 of actuator rod 342 is movably connected to a link 360 which is movably connected to member 362. Gripping arms 336 and 338 rotate in opposite directions about pivot point 364 to close or open upon tissue. When actuator rod 342 moves in the proximal direction, gripping arms 336 and 338 close together. Upper gripping arm 338 comprises heater wire 340, such as a nichrome wire, which is thermally and electrically insulated from gripping arm 338 by insulator 366. Here, the distal portion 370 of heater wire 340 is spot welded to the exterior surface 372 of gripping arm 338. The interior surface 374 of gripping arm 336 is preferably insulated, for example, with a silicone polymeric insulator. Heater wire 340 is operatively connected through wire 376 to a power source (not shown) and/or switch 352.

Figure 23:
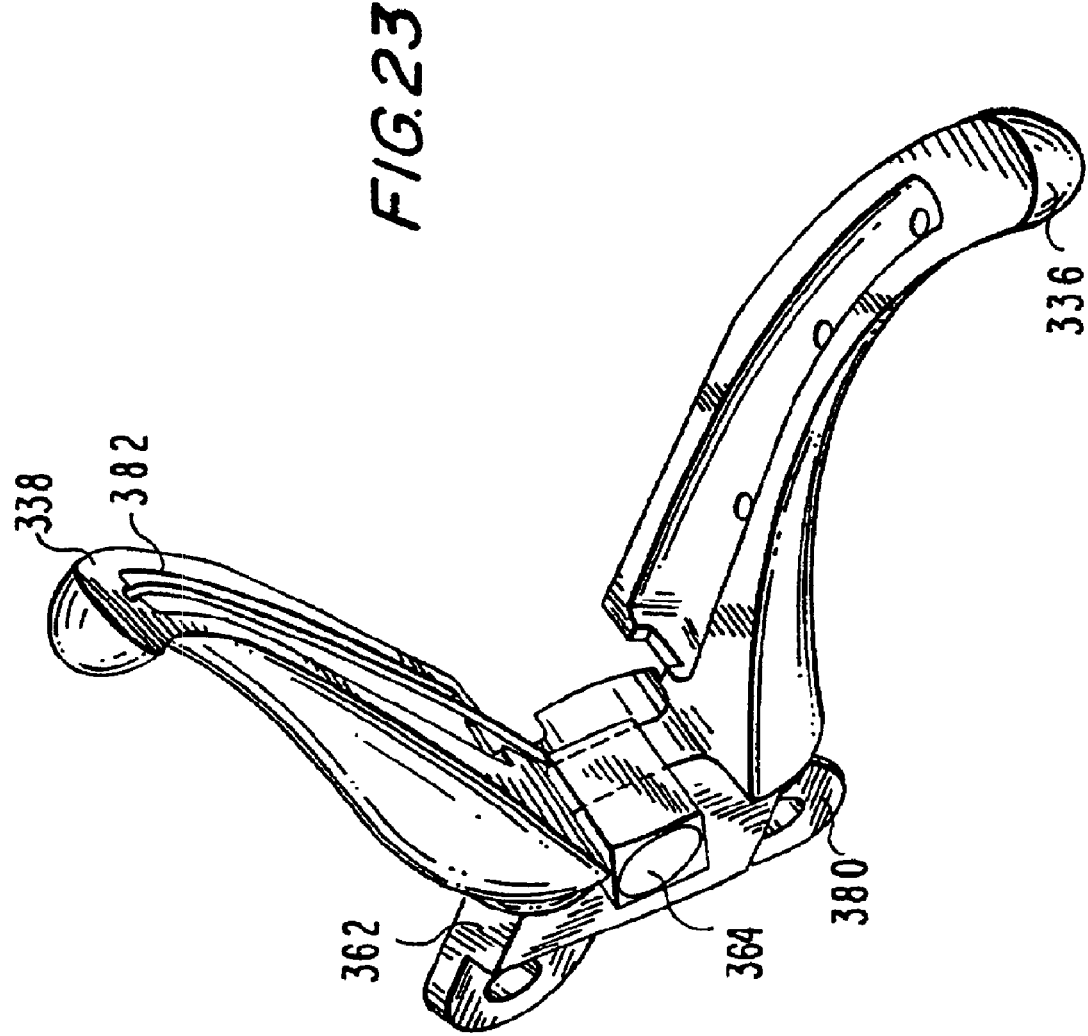
FIG. 23 is a partially cross-sectional schematic detail of an embodiment of the distal end shown in FIG. 22.

A detail of FIG. 22 is shown in FIG. 23, where the relationship between gripping arms 336 and 338 can be better appreciated, especially for he curved embodiment shown.

Member 362 and lower gripping arm 336 are integral and cooperatively arranged with upper gripping arm 338 and member 380 around pivot 364. The interior surfaces 382 and 374 of gripping arms 338 and 336, respectively each having polymeric insulation inserts.

As has been shown, the materials and the principles described for the tip design of the forceps can be modified slightly and applied to the clamp and to the laparoscopic grasper. Just as the design can be adjusted to a clamp and to a laparoscopic grasper, it can be applied to virtually any hand-held surgical instrument.

A monopolar RF version of a hook dissector is used in laparoscopic surgery. The embodiments of the invention shown in FIGS. 24 and 25 comprise a surgical dissecting instrument in the form of a hook, and this hook offers safety advantages over the RF version since the heating effect is confined to the tissue caught up in the hook. The heating element, preferably a nichrome wire, is situated on the inner surface of the hook so that tissue is compressed against the heater wire when tissue is "hooked" with the instrument.

Figure 24:
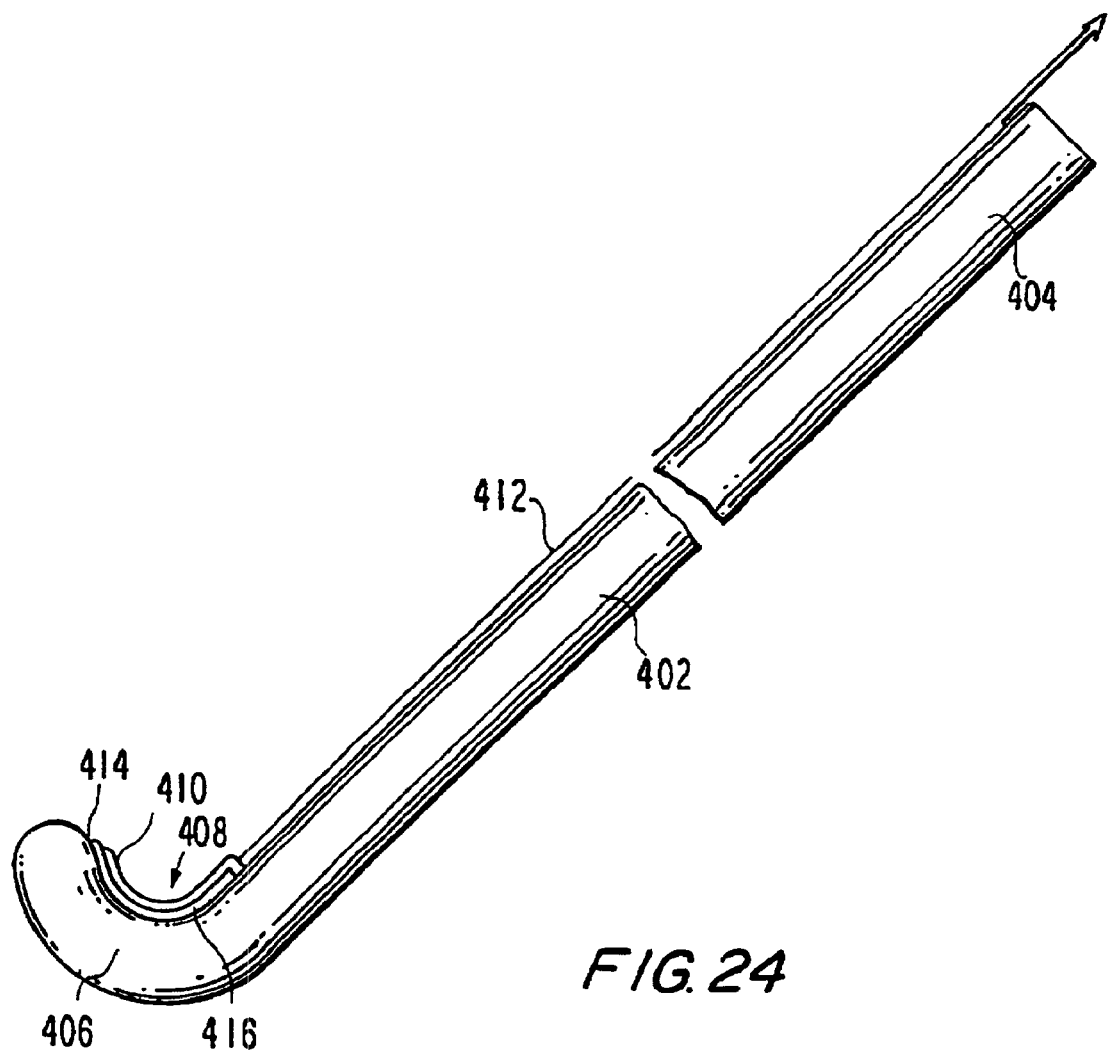

The instrument shown in FIG. 24 comprises an elongated member 402 having a proximal end 404, optionally textured to facilitate gripping, and a distal, hooked end 406. The interior surface 408 of hooked end 406 comprises a heater wire 410, which is operatively connected through wire 412 to a power source (not shown). The distal end 414 of heater wire 410 can be spot welded to hooked end 406, which provides a return path for electricity to the heater wire. Isolative material 416 between heater wire 410 and hooked end 406 thermally and electrically insulates heater wire 410. Optionally, insulation material 416 comprises a polymeric material in the form of a sleeve.

Elongated member 402 preferably comprises a physiologically acceptable, sterilizable metal such as stainless steel. Non-conductive rigid materials can be used so long as a pathway for electricity from the distal end heater wire 410 is provided.

In FIG. 25 an elongated member 430 has a proximal end 432, optionally textured, and a distal, hooked end 434. The lateral interior surface 436 of hooked end 434 comprises a heater wire 438. Heater wire 438 extends from a spot weld 446 into distal end 434 to a looping point 440 and then proximally. Through spot weld 446 heater wire 438 is in electrical connection with elongated member 430. Elongated member 430 is connected to one pole of a power source (not shown). The other end of heater wire 438 extending in the proximal direction after looping point 440 extends to wire 442 through an electrically and/or thermally shielded pathway 444. Wire 442 is connected to the other pole of the power source.

Elongated member 430 comprises a rigid, or substantially rigid, physiologically acceptable, sterilizable material. Useful materials include stainless steel and other conducting metals or alloys. It is within the scope of the invention that the distal portion of elongated member 430 could be comprised of a rigid or substantially rigid non-conducting material such as a suitable polymer, for example, polystyrene or an ABS polymer or copolymer It is intended that all matter contained in the above description and shown in the accompanying drawings shall be interpreted as illustrative and not in a limiting sense. Also, it is understood that the following claims are intended to cover all of the generic and specific features of the invention herein described and all statements of the scope of the invention which, as a matter of language, might be said to fall therebetween.

We claim:

1. A body tissue cutting device comprising:

a handle section and a first and second grasping arms extending from the handle section, said first and second grasping arms being resiliently mounted to the handle section to allow closure of the grasping arms by hand, said first and second grasping arms each having a proximal end and a distal end with a grasping face disposed on the grasping end of each grasping arm, said grasping face on each grasping arm aligned to meet the grasping face of the other grasping arm upon closure of the grasping arms; and a wire disposed upon the grasping face of the first grasping arm so that it lies between the grasping face of the first grasping arm and the grasping face of the second grasping arm upon closure of the grasping arms, said wire being operably connected to a source of electrical power, said wire being secured to the distal end of the first grasping arm and extending proximally over the grasping face of the first grasping arm toward the proximal end of the first grasping arm, wherein the grasping face of the first grasping arm has a resilient surface between the wire and the grasping face of the arm.

2. The device of claim 1 further comprising:

a sleeve covering the distal end of the first grasping arm, thereby forming a surface on the grasping face of the first grasping arm, said sleeve being separated from the distal end of the first grasping arm by a small fluid-filled gap.

3. The device of claim 1 further comprising:

a resilient sleeve covering the distal end of the second grasping arm, thereby forming a resilient surface on the grasping face of the second grasping arm.

4. The device of claim 1 further comprising:

a resilient surface on the grasping face of each of the first and second grasping arms.

5. The device of claim 1 further comprising:

a sleeve covering the distal end of the first grasping arm, thereby forming a surface on the grasping face of the first grasping arm, between the wire and the grasping face of the arm, said sleeve being distanced from the distal end by a small fluid-filled gap, and a resilient sleeve covering the distal end of the second grasping arm, thereby forming a resilient surface on the grasping face of the second grasping arm.

6. The device of claim 1 wherein the grasping arms comprise a pair of tweezers.

7. The device of claim 1 wherein the grasping arms comprise a forceps.

8. A medical device comprising:

a pair of tweezers characterized by a first grasping arm and a second grasping arm, each of said grasping arms having a proximal end and a distal end, said first grasping arm having a first gripping face disposed on the distal end thereof, said second grasping arm having a second gripping face disposed on the distal end thereof, said gripping faces defining surfaces generally perpendicular to a plane defined by the grasping arms, said surfaces being movable into apposition with each other upon closing of the tweezers;

a first layer of resilient material disposed on the gripping face of the first grasping arm;

a second layer of resilient material disposed on the gripping face of the second grasping arm; and a wire disposed between the first and second layers of resilient material so as to be trapped between the gripping faces of the first and second grasping arms upon closing of the tweezers.

9. A medical device comprising:

a pair of forceps characterized by a first grasping arm and a second grasping arm, each of said grasping arms having a proximal end and a distal end, each of said grasping arms being rotatably fixed to the other at a midpoint thereof, said first grasping arm having a first gripping face disposed on the distal end thereof, said second grasping arm having a second gripping face disposed on the distal end thereof, said gripping faces defining surfaces generally perpendicular to a plane defined by the grasping arms, said surfaces being movable into apposition with each other upon closing of the forceps;

a first layer of resilient material disposed on the gripping face of the first grasping arm;

a second layer of resilient material disposed on the gripping face of the second grasping arm;

a wire disposed between the first and second layers of resilient material so as to be trapped between the gripping faces of the first and second grasping arms upon closing of the forceps.

10. A medical device comprising:

a laparoscopic grasper characterized by a first grasping arm and a second grasping arm, each of said grasping arms having a proximal end and a distal end, each of said grasping arms being rotatable relative to the other about a point near the distal end thereof, said grasping arms being adapted to be inserted into the body and to be rotatably opened and closed upon each other within the body, said first grasping arm having a first gripping face disposed on the distal end thereof, said second grasping arm having a second gripping face disposed on the distal end thereof, said gripping faces defining surfaces generally perpendicular to a plane defined by the grasping arms, and said surfaces being movable into apposition with each other upon closing of the graspers;

a first layer of resilient material disposed on the gripping face of the first grasping arm;

a second layer of resilient material disposed on the gripping face of the second grasping arm; and a wire disposed between the first and second layers of resilient material so as to be trapped between the gripping faces of the first and second grasping arms upon closing of the graspers.

* * * * *